US012616206B2

(12) United States Patent
Haddadi et al.

(10) Patent No.: US 12,616,206 B2
(45) Date of Patent: May 5, 2026

(54) GRAPHENE-SILVER NANOCOMPOSITES AND USES FOR SAME AS AN ANTIMICROBIAL COMPOSITION

(71) Applicant: ZENTEK LTD., Guelph (CA)

(72) Inventors: Seyyedarash Haddadi, Ontario (CA); Colin Van Der Kuur, Kelowna (CA); Joseph Korkis, Burlington (CA); Deepak Sridhar, Guelph (CA)

(73) Assignee: ZENTEK LTD., Guelph (CA)

( * ) Notice: Subject to any disclaimer, the term of this patent is extended or adjusted under 35 U.S.C. 154(b) by 327 days.

(21) Appl. No.: 18/245,971

(22) PCT Filed: Sep. 20, 2021

(86) PCT No.: PCT/CA2021/051308
§ 371 (c)(1),
(2) Date: Mar. 20, 2023

(87) PCT Pub. No.: WO2022/056645
PCT Pub. Date: Mar. 24, 2022

(65) Prior Publication Data
US 2024/0041045 A1      Feb. 8, 2024

Related U.S. Application Data

(60) Provisional application No. 63/161,873, filed on Mar. 16, 2021, provisional application No. 63/128,993, filed on Dec. 22, 2020, provisional application No. 63/081,301, filed on Sep. 21, 2020.

(51) Int. Cl.
| | |
|---|---|
| A01N 59/16 | (2006.01) |
| A01N 25/34 | (2006.01) |
| A01N 59/20 | (2006.01) |
| A01P 1/00 | (2006.01) |
| A01P 3/00 | (2006.01) |
| A61L 9/01 | (2006.01) |
| A62B 23/02 | (2006.01) |
| B01D 46/00 | (2022.01) |
| C01B 32/194 | (2017.01) |
| C01B 32/198 | (2017.01) |
| C09D 5/14 | (2006.01) |
| C09D 7/62 | (2018.01) |

(52) U.S. Cl.
CPC ............. *A01N 59/16* (2013.01); *A01N 25/34* (2013.01); *A01N 59/20* (2013.01); *A01P 1/00* (2021.08); *A01P 3/00* (2021.08); *A61L 9/01* (2013.01); *A62B 23/02* (2013.01); *B01D 46/0028* (2013.01); *C01B 32/194* (2017.08);

*C01B 32/198* (2017.08); *C09D 5/14* (2013.01); *C09D 7/62* (2018.01); *A61L 2209/14* (2013.01); *B01D 2279/65* (2013.01); *C01P 2004/61* (2013.01)

(58) Field of Classification Search
None
See application file for complete search history.

(56) References Cited

PUBLICATIONS

Zhang et al.( Interfacial Engineering of Bimetallic Ag/Pt Nanoparticles on Reduced Graphene Oxide Matrix forEnhanced Antimicrobial Activity, ACS Applied Materials & Interfaces (2016 ), 8(13), 8834-8840). (Year: 2016).*
Liu et al. Development and Antibacterial Performance of NovelPolylactic Acid-Graphene Oxide—Silver Nanoparticle Hybrid Nanocomposite Mats Prepared by ( ACS Biomaterials Science & Engineering 2017, vol. 3 No. 3, pp. 471-486). (Year: 2017).*
Jankauskaite et al. Bactericidal effect of graphene oxide /Cu/Ag nanoderivatives against *Escherichia coli*, Pseudomonas aerugi(International Journal of Pharmaceutics (Amsterdam, Netherlands) (2016 ), 511(1), 90-97 Coden: Ijphde; ISSN: 0378- 5173). (Year: 2016).*
Du, T. et al., "Antiviral Activity of Graphene Oxide—Silver Nanocomposites by Preventing Viral Entry and Activation of the Antiviral Innate Immune Response," ACS Applied Bio Materials, vol. 1, pp. 1286-1293, 2018.
Gómez de Saravia, S.G. et al., "Anti-adhesion and antibacterial activity of silver nanoparticles and graphene oxide—silver nanoparticle composites," Revistamatéria, vol. 25, No. 02, 2019, 9 pages.
Wierzbicki, M. et al., "Grapahene Oxide in a Composite with Silver Nanoparticles Reduces the Fibroblast and Endothelial Cell Cytotoxicity of an Antibacterial Nanoplatform," Nanoscale Research Letters, vol. 14, No. 320, 2019, 11 pages.
International Search Report mailed Nov. 23, 2021, issued in International Application No. PCT/CA2021/051308, filed Sep. 20, 2021, 3 pages.
Written Opinion mailed Nov. 23, 2021 in International Application No. PCT/CA2021/051308, filed Sep. 20, 2021, 7 pages.

* cited by examiner

*Primary Examiner* — Alton N Pryor
(74) *Attorney, Agent, or Firm* — Christensen O'Connor Johnson Kindness PLLC

(57) ABSTRACT

The present invention relates to antimicrobial compositions comprising graphene-silver cation nanocomposites and uses for same as an antimicrobial agent. The antimicrobial agent is particularly useful as a disinfectant or for use as a coating to confer antimicrobial activity to a substrate. The antimicrobial agent can further be used to enhance filtration efficiency in PPE, face masks, and filters in air filtration (HVAC) systems, and other airflow membranes and filters to reduce the transmission of microbial pathogens.

17 Claims, 22 Drawing Sheets

Possible Chemical Reactions and Formulations:

$$NaOH \rightarrow Na^+ + OH^-$$

$$AgNO_3 \rightarrow Ag^+ + NO_3^-$$

$$Ag^+ + OH^- \rightarrow AgOH$$

$$-OH + AgOH \rightarrow -O - Ag$$

| Element | Weight% | Atomic% |
|---------|---------|---------|
| C K | 89.31 | 91.16 |
| O K | 12.29 | 9.41 |
| S K | -1.34 | -0.51 |
| Mn K | -0.25 | -0.06 |
| Totals | 100.00 | 100.00 |

| Element | Weight% | Atomic% |
|---------|---------|---------|
| C K | 84.16 | 87.50 |
| O K | 16.24 | 12.68 |
| S K | -0.52 | -0.20 |
| Mn K | 0.11 | 0.02 |
| Totals | 100.00 | |

| Element | Weight% | Atomic% |
|---------|---------|---------|
| C K | 80.94 | 84.81 |
| O K | 19.58 | 15.40 |
| S K | -0.55 | -0.22 |
| Mn K | 0.03 | 0.01 |
| Totals | 100.00 | |

| Element | Weight% | Atomic% |
|---|---|---|
| C K | 26.38 | 50.07 |
| N K | 4.42 | 7.20 |
| O K | 20.37 | 29.03 |
| S K | 6.76 | 4.80 |
| Mn K | 0.02 | 0.01 |
| Ag L | 42.05 | 8.89 |
| Totals | 100.00 | 100.00 |

| Element | Weight% | Atomic% |
|---------|---------|---------|
| C K | 70.72 | 78.81 |
| N K | 8.18 | 7.82 |
| O K | 15.28 | 12.78 |
| S K | -0.45 | -0.19 |
| Mn K | 0.03 | 0.01 |
| Ag L | 6.25 | 0.78 |
| Totals | 100.00 | 100.00 |

| Element | Weight% | Atomic% |
|---------|---------|---------|
| C K | 27.27 | 59.97 |
| N K | 7.52 | 14.18 |
| O K | 4.37 | 7.22 |
| S K | 6.37 | 5.25 |
| Mn K | 0.22 | 0.10 |
| Ag L | 54.25 | 13.28 |
| Totals | 100.00 | 100.00 |

| Element | Weight% | Atomic% |
|---------|---------|---------|
| C K | 74.72 | 82.00 |
| N K | 5.50 | 5.18 |
| O K | 15.04 | 12.39 |
| S K | -0.45 | -0.18 |
| Mn K | -0.08 | -0.02 |
| Ag L | 5.27 | 0.64 |
| Totals | 100.00 | 100.00 |

Rough                    Fine

Fine

Rough

| Sample ID | Spot | C | O | Ag | P | Cl | Al | F | Ca |
|---|---|---|---|---|---|---|---|---|---|
| Rough - high loading | MAP sum | 65.5 | 33.1 | 1.3 | 0.0 | 0.0 | 0.0 | 0.0 | 0.1 |
| | S-18 | 72.0 | 27.9 | 0.1 | 0.0 | 0.0 | 0.0 | 0.0 | 0.0 |
| | S-19 | 66.4 | 30.7 | 3.0 | 0.0 | 0.0 | 0.0 | 0.0 | 0.0 |
| | S-20 | 76.7 | 20.8 | 2.5 | 0.0 | 0.0 | 0.0 | 0.0 | 0.0 |
| | S-21 | 79.9 | 19.1 | 1.0 | 0.0 | 0.0 | 0.0 | 0.0 | 0.0 |
| | S-22 | 82.7 | 15.5 | 1.8 | 0.0 | 0.0 | 0.0 | 0.0 | 0.0 |
| | AVG | 73.9 | 24.5 | 1.6 | 0.0 | 0.0 | 0.0 | 0.0 | 0.0 |
| Fine - high loading | S-12 | 70.3 | 28.9 | 0.8 | 0.0 | 0.0 | 0.0 | 0.0 | 0.0 |
| | S-13 | 70.2 | 25.9 | 3.5 | 0.0 | 0.4 | 0.0 | 0.0 | 0.0 |
| | S-14 | 69.2 | 28.4 | 2.1 | 0.0 | 0.3 | 0.0 | 0.0 | 0.0 |
| | S-15 | 73.7 | 25.9 | 0.4 | 0.0 | 0.0 | 0.0 | 0.0 | 0.0 |
| | S-16 | 69.3 | 28.3 | 2.4 | 0.0 | 0.0 | 0.0 | 0.0 | 0.0 |
| | MAP sum | 64.2 | 31.4 | 2.4 | 0.0 | 0.2 | 0.0 | 1.9 | 0.0 |
| | AVG | 69.5 | 28.1 | 1.9 | 0.0 | 0.2 | 0.0 | 0.3 | 0.0 |

Figure 13

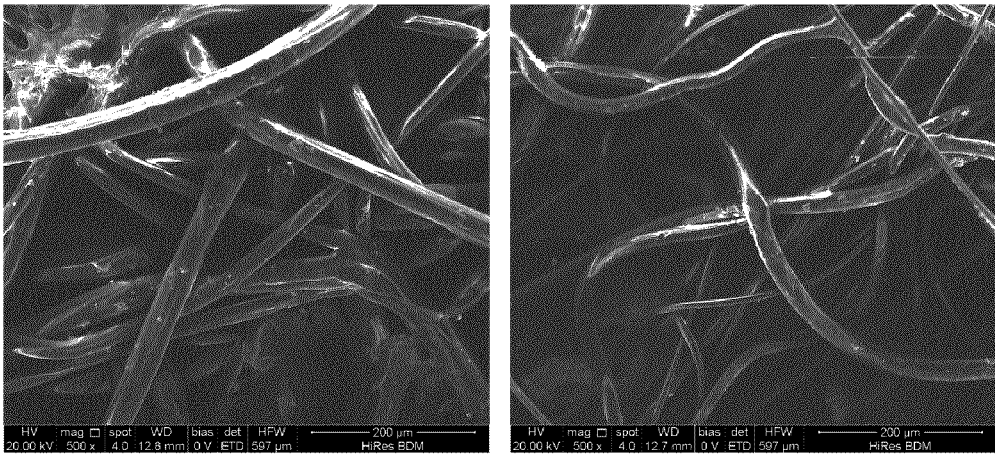
Figure 14A                    Figure 14B
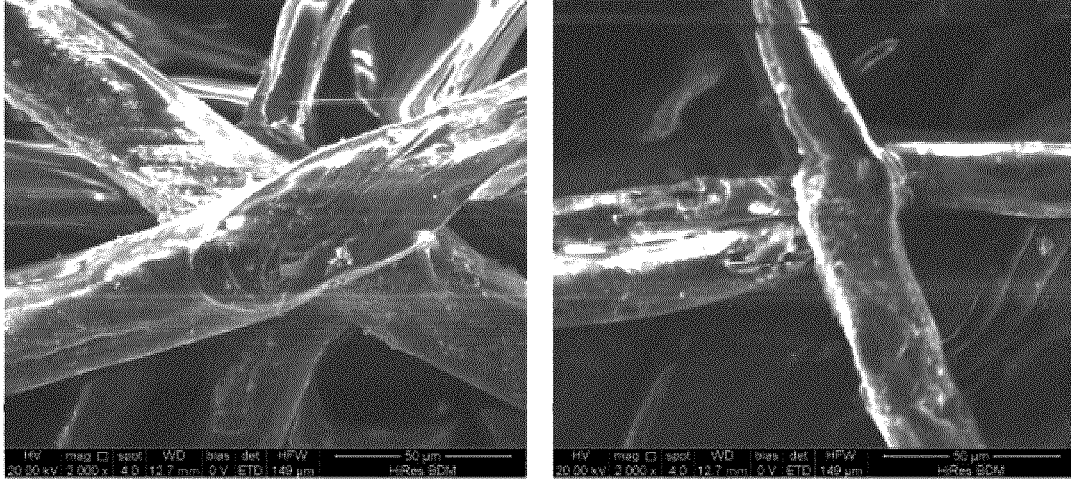
Figure 14C                    Figure 14D

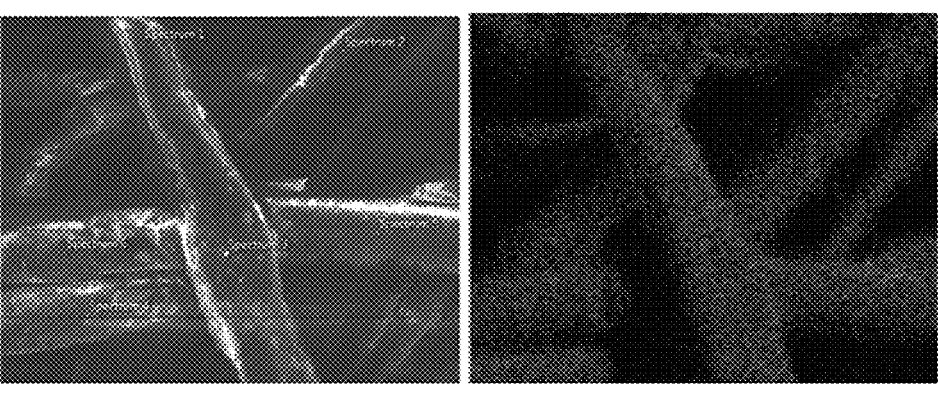
Figure 15A                    Figure 15B
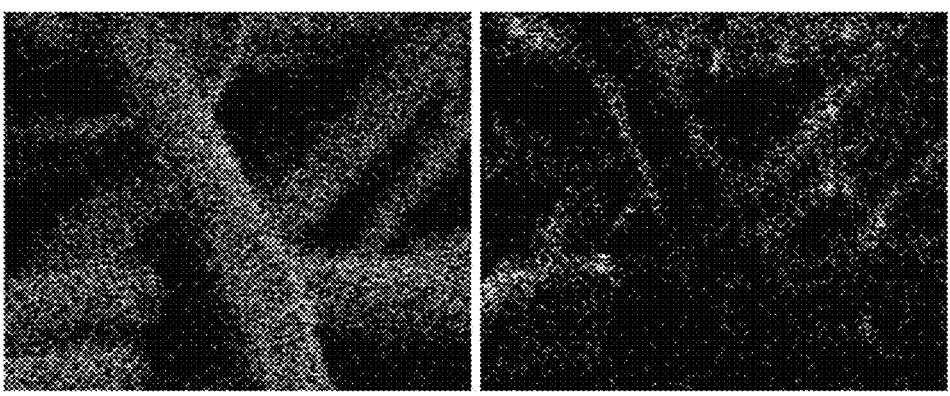
Figure 15C                    Figure 15D
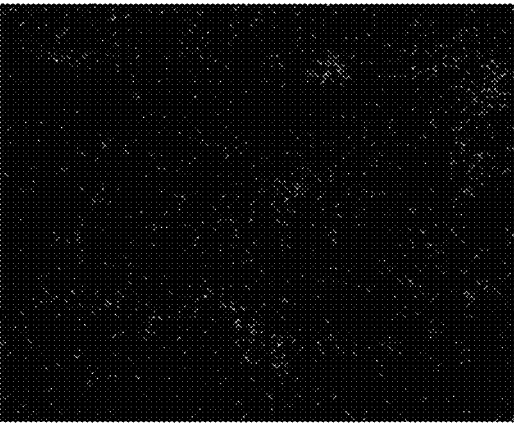
Figure 15E

| Sample ID | Spot | C | O | Ag | P | Cl | Al | F | Ca |
|---|---|---|---|---|---|---|---|---|---|
| Rough - low loading | S-7 | 69.3 | 28.8 | 1.6 | 0.2 | 0.1 | 0.0 | 0.0 | 0.0 |
| | S-8 | 71.1 | 28.6 | 0.1 | 0.0 | 0.0 | 0.1 | 0.0 | 0.0 |
| | S-9 | 69.6 | 24.1 | 5.2 | 0.7 | 0.3 | 0.0 | 0.0 | 0.0 |
| | S-10 | 69.6 | 29.6 | 0.8 | 0.0 | 0.0 | 0.0 | 0.0 | 0.0 |
| | S-11 | 74.8 | 24.9 | 0.3 | 0.0 | 0.0 | 0.0 | 0.0 | 0.0 |
| | MAP sum | 64.2 | 35.1 | 0.7 | 0.0 | 0.0 | 0.1 | 0.0 | 0.0 |
| | AVG | 69.8 | 28.5 | 1.5 | 0.2 | 0.1 | 0.0 | 0.0 | 0.0 |
| Fine - low loading | MAP sum | 63.0 | 27.2 | 0.4 | 0.0 | 0.0 | 0.2 | 9.1 | 0.1 |
| | S-1 | 75.7 | 24.1 | 0.0 | 0.0 | 0.0 | 0.2 | 0.0 | 0.0 |
| | S-2 | 74.3 | 20.7 | 0.9 | 0.0 | 0.0 | 0.4 | 3.7 | 0.0 |
| | S-3 | 68.7 | 29.2 | 1.8 | 0.0 | 0.0 | 0.0 | 0.0 | 0.2 |
| | S-4 | 72.4 | 27.6 | 0.0 | 0.0 | 0.0 | 0.0 | 0.0 | 0.0 |
| | S-5 | 70.1 | 29.7 | 0.0 | 0.0 | 0.0 | 0.1 | 0.0 | 0.0 |
| | S-6 | 69.6 | 24.8 | 0.5 | 0.0 | 0.0 | 0.0 | 5.1 | 0.0 |
| | AVG | 70.5 | 26.2 | 0.5 | 0.0 | 0.0 | 0.1 | 2.6 | 0.0 |

Figure 18

GRAPHENE-SILVER NANOCOMPOSITES AND USES FOR SAME AS AN ANTIMICROBIAL COMPOSITION

CROSS REFERENCE TO RELATED APPLICATIONS

This application is the U.S. national phase of PCT/CA2021/051308 filed on Sep. 20, 2021, which claims the benefit of U.S. Patent Application No. 63/161,873, filed Mar. 16, 2021; U.S. Patent Application No. 63/128,993, filed Dec. 22, 2020; and U.S. Patent Application No. 63/081,301, filed Sep. 21, 2020, the disclosure of each of which is expressly incorporated herein by reference in its entirety.

FIELD OF THE INVENTION

The present invention relates to the field of antimicrobial agents and, in particular, to graphene-silver nanocomposites and compositions thereof for use in conferring antimicrobial activity to a substrate.

BACKGROUND OF THE INVENTION

Microorganisms (or microbes) are single cell, cell cluster, or multicellular microscopic (or macroscopic) organisms including but not limited to, bacteria, fungi, and viruses. Pathogenic microbes have the potential to cause a multitude of infectious diseases through various modes of transmission including by contact, touch, or airborne transmission. For example, contamination of surfaces with one or more types of microorganisms, the transfer of microorganisms between surfaces, and/or the aerosol transfer of microbes in the air, can lead to transmission of illness and disease.

Infectious diseases caused by pathogenic microbes continue to be a global issue. In recent years, there have been widespread outbreaks of Swine Flu, Ebola virus, Zika virus, norovirus, severe acute respiratory syndrome (SARS), Middle East respiratory syndrome (MERS), and most recently coronavirus disease 19 (COVID-19) which has been declared a pandemic by the World Health Organization.

Pathogenic microbes are most commonly spread throughout a community by host-to-host transfer, including through respiratory droplets; close, prolonged personal contact; and touching an infected area, then touching the mouth, nose or eyes before washing hands. Efforts to stop the transmission of infection have required the use of antimicrobial disinfectants, physical distancing from infected hosts, and physical protective barriers such as the wearing of face masks, gloves, and protective clothing, otherwise known as personal protective equipment (PPE). Pathogenic microbes have also been shown to spread as aerosols and can spread through airborne transmission. Studies of pathogen transmission in enclosed spaces have shown that recirculated air may further result in the spreading of pathogenic microbes.

Current PPE are typically single-use, or re-usable, materials that are designed to create a physical barrier to protect the wearer of the PPE from exposure to the pathogenic microbe. Similarly, current air filtration systems rely on materials that physically filter out dust, pollen and other airborne agents. Materials that filter out a pathogenic microbe, or altogether physically block exposure to the pathogenic microbe, have had limited effectiveness and have raised new issues in transmission. For example, it has been found that many disease-causing pathogenic microbes are smaller in size than the filtering-size of most filter media used for face masks. In this regard, the virus causing COVID-19 (SARS-CoV-2 virus) has been identified as having a particle size of 0.125 μm, which is much smaller than the size of the particles that are filtered by most face mask materials including N95 masks. Reducing the filtering-size of the filter media is further not possible without compromising air flow and exchange to allow the wearer to breathe.

A further risk of transmission also exists from contact with contaminated substrate surfaces and materials. Disease-causing microbes typically remain viable on filter media and other substrate materials for a period of time that can range between hours to days. For example, the SARS-CoV-2 virus has been shown to remain viable on materials for 3 days, and the H1N1 virus was shown to remain on protective materials for 6 days. As a result, substrate surfaces or protective materials that have been used and discarded, can remain contaminated for relatively long periods of time and, therefore, carry the risk of leading to the secondary transmission of the pathogen into the environment.

A need exists for compositions and/or materials that protect against pathogen transmission on multiple levels, namely, compositions and/or materials that physically block, trap, or immobilize the pathogen, as well as being able to destroy the pathogen to prevent secondary transmission. Moreover, a need exists for antimicrobial compositions and/or materials that are amenable to being applied to substrate surfaces, or processed into, functional products such as PPE and filter membranes in ventilation systems, to confer antimicrobial activity.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a graphene-silver nanocomposite and uses for same as an antimicrobial composition. In accordance with one aspect of the invention, there is described an antimicrobial nanocomposite comprising graphene oxide (GO) and cationic silver ($Ag^+$) moieties bound to the GO.

In accordance with another aspect of the invention, there is described an antimicrobial nanocomposite comprising GO and $Ag^+$ bound in a complex to the GO.

In accordance with another aspect of the invention, there is described an antimicrobial formulation comprising a GO-$Ag^+$ nanocomposite and a solvent, a carrier, a diluent, and/or a dispersant.

In accordance with another aspect of the invention, there is described a use of a GO-$Ag^+$ nanocomposite as an antimicrobial coating for inactivating pathogenic microbes on a substrate.

In accordance with another aspect of the invention, there is described a method for conferring antimicrobial activity to a substrate, comprising: (a) dispersing a nanocomposite comprising graphene oxide (GO) and silver cations ($Ag^+$) bonded thereto, in deionized water, ethanol, or deionized water and ethanol; and (b) applying the nanocomposite dispersion to the substrate.

In accordance with another aspect of the invention, there is described a personal protective equipment (PPE) comprising an antimicrobial nanocomposite coated thereon, wherein the nanocomposite comprises graphene oxide (GO) and silver cations ($Ag^+$) bonded thereto.

In accordance with another aspect of the invention, there is described a face mask comprising an antimicrobial nanocomposite coated thereon, wherein the nanocomposite comprises graphene oxide (GO) and silver cations ($Ag^+$) bonded thereto.

In accordance with another aspect of the invention, there is described an airflow membrane filter comprising an antimicrobial nanocomposite coated thereon, wherein the nanocomposite comprises graphene oxide (GO) and silver cations ($Ag^+$) bonded thereto.

BRIEF DESCRIPTION OF THE DRAWINGS

These and other features of the invention will become more apparent in the following detailed description in which reference is made to the appended drawings.

FIG. 10A shows both rough and fine sides, FIG. 10B shows the fine side, and FIG. 10C shows the rough side.

FIG. 11A shows the electron image, FIG. 11B shows C detection, FIG. 11C shows the peak identification for the targeted elements (C, O, Ag), FIG. 11D shows O detection, FIG. 11E shows Ag detection, and FIG. 11F shows peaks identification for the targeted elements (C, O, Ag).

FIG. 12A shows the electron image, FIG. 12B shows C detection, FIG. 12C shows the peaks identification for the targeted elements (C, O, Ag), FIG. 12D shows O detection, FIG. 12E shows Ag detection, and FIG. 12F shows the peak identification for the targeted elements (C, O, Ag).

FIG. 13 is a Table showing the elemental composition of both rough and fine sides of a fabric sample with GO-$Ag^+$ nanocomposite at a high loading concentration of 5 g/L.

FIGS. 14A, 14B, 14C, 14D are SEM images of both sides of a fabric sample coated with GO-$Ag^+$ nanocomposite at a low loading concentration of 0.5 g/L. FIG. 14A shows the rough side at 500×, FIG. 14B shows the fine side at 500×, FIG. 14C shows the rough side at 2000×, and FIG. 14D shows the fine side at 2000×.

FIGS. 15A, 15B, 15C, 15D, 15E are EDX analysis images of the fine side of a fabric sample with GO-$Ag^+$ nanocomposite at a low loading concentration of 0.5 g/L. FIG. 15A shows the electron image, FIG. 15B shows C detection, FIG. 15C shows O detection, FIG. 15D shows F detection, and FIG. 16E shows Ag detection.

FIG. 16A shows the peak identification for the targeted elements (C, O, F, Ag), FIG. 16B shows peak identification for the targeted elements (C, O, F, Ag).

FIG. 17A shows the electron image, FIG. 17B shows C detection, FIG. 17C shows the peak identification for the targeted elements (C, O, Ag), FIG. 17D shows O detection, FIG. 17E shows Ag detection. FIG. 17F shows the peak identification for the targeted elements (C, O, Ag).

FIG. 18 is a Table showing the elemental composition of both rough and fine sides of a fabric sample with GO-$Ag^+$ nanocomposite at a low loading concentration of 0.5 g/L.

DETAILED DESCRIPTION OF THE INVENTION

Figure 1:
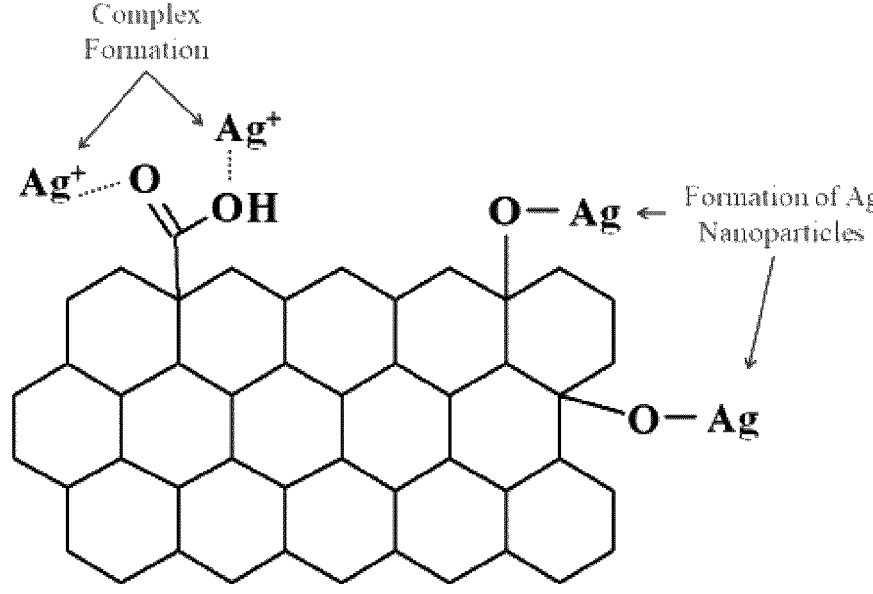
FIG. 1 is a schematic illustration of $Ag^+$ complex formation with oxygen-containing functional groups of GO and the formation of Ag nanoparticles on the surface of GO nanosheets.

Two-dimensional graphene oxide (GO) has shown promise as a nanomaterial for various applications, including biomedical applications, due to its lateral size and the colloidal properties of the nanosheets. The antibacterial effect of GO has also been described, specifically as a supporting and stabilizing agent for antibacterial compounds, for example, silver nanoparticles (Ag NPs). More specifically, GO-AgNP nanocomposites have been thought to enhance the antibacterial effect of AgNPs by immobilizing the AgNPs on GO to prevent the movement of the nanoparticles.

While GO-AgNP nanocomposites have been shown to have antibacterial effects, the use of GO-AgNP nanocomposites for broad-spectrum antimicrobial applications has been shown to have a number of limitations, including for example its instability in water affecting the ability of GO-AgNP to effectively release the antimicrobially active form of $Ag^+$ ions. As a result, additional chemicals, solvents, and post-processing are typically required to stabilize GO-AgNP nanocomposites for use. According to certain embodiments of the present invention, GO-$Ag^+$ nanocomposites that comprise GO nanosheets with cationic silver ($Ag^+$) moieties bound to the GO are described that are stable in water without the need for additional chemicals, solvents or post-processing.

According to certain embodiments of the present invention, GO-$Ag^+$ nanocomposites are described that unexpectedly exhibit potent antibacterial as well as antifungal and/or antiviral efficacy. Moreover, in further embodiments, GO-$Ag^+$ nanocomposites are described that unexpectedly exhibit potent antimicrobial efficacy against AMR and/or MDR pathogens. Without being bound by theory, it is contemplated that GO produces a high surface area for the attachment of $Ag^+$ cations and further stabilizes the $Ag^+$ cations on the GO-$Ag^+$ nanocomposite. In this way, the GO nanosheets provide a stabilizing framework for the $Ag^+$ cations which cause oxidative stress to the pathogen. Additionally, the functional oxygen groups on GO in combination with the physical shearing effect of the sharp edges of the graphene on a pathogen, are further believed to work synergistically with the antimicrobial effect of the $Ag^+$ cations. Specifically, it is believed that GO envelopes and captures the pathogen due to its affinity to carbon, and further pierces the cell membrane to deliver oxidative stress to the pathogen due to the $Ag^+$.

According to embodiments, the in-situ bonding of cationic silver ($Ag^+$) to GO facilitates a uniformly distributed complex, unlike the mixing of pre-formed nanoparticles with GO which often forms agglomerations. This provides enhanced surface area of the formed active material and an ability to effectively use $Ag^+$ to create oxidative stress to the pathogen. According to embodiments, the GO and $Ag^+$ components of the GO-$Ag^+$ nanocomposites have a synergistic antimicrobial efficacy. In certain embodiments, the GO-$Ag^+$ nanocomposites exhibit broad spectrum antimicrobial efficacy at a concentration less than 0.1 µg/mL, 0.08 µg/mL, 0.06 µg/ml, 0.04 µg/mL, 0.02 µg/mL, 0.009 µg/mL, or 0.007 µg/mL.

In certain embodiments, the GO-$Ag^+$ nanocomposites comprise a nanocomposite formed by graphene oxide (GO) sheets with silver cation ($Ag^+$) moieties bound to the GO. In further embodiments, the silver cation ($Ag^+$) moieties are bound to the GO as complexes. In further embodiments, the nanocomposite comprises GO sheets with a combination of $Ag^+$ moieties bound to the GO by complex bonds, as well as silver nanoparticles (Ag NP) chemically bonded and in some cases physically adsorbed onto the GO thereto. According to certain embodiments, the majority of the attached silver is in the cationic form ($Ag^+$) and is bound to the GO. According to some embodiments, the majority of the attached silver is in the cationic form and bound to the GO as complexes. In further embodiments, the majority of the attached silver is in the cationic form and bound to the GO as complexes and further comprises a small amount of silver nanoparticles. The silver nanoparticles are formed due to reduction of the cationic form that accompanies the oxidation of certain functional groups on the GO. Such functional groups may include epoxy, hydroxyl, carboxylic, carbonyl, quinone or any specific functional group introduced on the surface during the preparation of GO. In certain embodiments, the $Ag^+$ may be attached to the GO surface by the addition of functional groups on the GO, including for example N or P functional groups. According to certain embodiments described herein, the GO-$Ag^+$ nanocomposites comprise complexed GO-$Ag^+$. In other embodiments, the GO-$Ag^+$ nanocomposites comprise complexed GO-$Ag^+$ and free $Ag^+$ cations. According to further embodiments described herein, the GO-$Ag^+$ nanocomposites comprise Ag in various chemical states such as Ag(0) or Ag(1) in salt, oxide or metal form. In certain embodiments, 50-98% of the attached silver is bonded to the GO by complex bonds. According to other embodiments, 65-85% of the attached silver is bonded by complex bonds. In further embodiments, 70% of the attached silver is bonded to the GO by complex bonds. In other embodiments, 85%-95% of the attached silver is bonded to the GO by complex bonds. In further embodiments, 90-95% of the attached silver is bonded to the GO by complex bonds.

In further embodiments, the GO sheets of the present invention have been made to have a sufficiently large surface area for other antimicrobial agents to be additionally combined, for example, the addition of one or more other metals such as $Cu^{2+}$ and/or $Zn^{2+}$ and/or $Au^{2+}$ cations, or a combination thereof, to the GO-$Ag^+$ nanocomposite. According to certain embodiments, the GO-$Ag^+$ nanocomposite further includes one or more other metal and metal-ligand complexes, for example, copper (e.g., copper ion, copper nanoparticles), gold (gold ion, gold nanoparticles), and/or zinc (zinc ion, zinc nanoparticles), or any combination thereof.

According to embodiments of the invention, the GO-$Ag^+$ nanocomposite compositions provide broad spectrum antimicrobial activity. In some embodiments, the described GO-$Ag^+$ nanocomposite compositions have potent antimicrobial activity against a bacterial pathogen, a viral pathogen, or a fungal pathogen, or any combination thereof. In further embodiments, the GO-$Ag^+$ nanocomposite compositions have antimicrobial activity against antimicrobial-resistant and/or multidrug-resistant microbial strains.

In certain embodiments of the invention, the GO-$Ag^+$ nanocomposite compositions are provided as formulations for inactivating a broad spectrum of pathogens on a variety of substrates. According to embodiments, formulations are provided that are useful for providing antimicrobial effects to a variety of surfaces. In several embodiments, the surface is a solid substrate including but not limited to countertops, door handles, faucets, telephones, cellphones, beds/bed frames, bed linens, medical equipment, computers, automobile-dash boards, components of chairs, various hand-held devices and equipment, writing instruments, surgical equipment, animal pens, kennels, and animal or livestock barn stalls.

Formulations of the GO-$Ag^+$ nanocomposite are provided, in certain embodiments, as a solution and/or suspension, and/or dispersion, and/or emulsion, that can be directly applied to a substrate surface to confer antimicrobial effect. According to certain embodiments, the formulation is applied as a disinfectant spray onto a high touchpoint substrate surface or enclosure. In certain embodiments, the substrate surface is a wall, or countertop, floors, bench, desk, or an animal or livestock barn stall, kennel, or pen for housing animals. In certain embodiments, the GO-$Ag^+$ nanocomposites described herein can be adhered or coated (e.g., adsorbed or conjugated) to the surface of an article of manufacture to confer antimicrobial properties to that article of manufacture. Certain embodiments of the invention relate to formulations of the nanocomposites of the present invention provided as a coating that can be applied to the surface of materials to confer antimicrobial properties to various products. According to certain embodiments, these products include face masks, PPE, environmental cleaning wipes and other sanitation-related products, counters, door handles, walls, filters in air filtration (HVAC) systems, and other airflow membranes and filters, to reduce the pathogenic activity of the microbial pathogens.

According to certain embodiments, the formulations described herein confer antimicrobial properties to a treated surface by directly deactivating/killing the microbe. In particular embodiments, the formulations further confer enhanced filtration efficiency to a treated substrate. According to such embodiments, the hydrophilicity of the GO-$Ag^+$ nanocomposite effectively attracts, retains, and/or immobilizes microbes on a treated substrate surface thereby inhibiting their passage through the treated substrate. According to further embodiments, the GO-$Ag^+$ nanocomposites allow microbes in saliva aerosols from an infected person, to adhere to the GO sheet while the $Ag^+$ causes oxidative stress on the microbe. This aspect of the GO-$Ag^+$ nanocomposites provide particular application in certain embodiments such as face masks, air filters, and membranes.

According to various embodiments, the formulations described herein confer highly antimicrobial properties to a treated surface that remain stable for prolonged periods of time. According to certain embodiments, the formulations of the GO-Ag$^+$ nanocomposites described herein kill (or otherwise inactivate) at least between 75-100% of pathogens on contact with the formulation. In a further aspect, such formulations are stable for at least 3 to 6 weeks post-application to kill (or otherwise inactivate) at least between 90-100% of pathogens on contact with the formulation. In other embodiments, the effect persists for up to 3 months. According to further embodiments, the effect persists for up to 2 months. In additional embodiments, the effect persists for up to 1 month.

Definitions

Unless defined otherwise, all technical and scientific terms used herein have the same meaning as commonly understood by one of ordinary skill in the art to which this invention belongs.

As used herein, the term "about" refers to an approximately +/−10% variation from a given value. It is to be understood that such a variation is always included in any given value provided herein, whether or not it is specifically referred to.

The use of the word "a" or "an" when used herein in conjunction with the term "comprising" may mean "one", but it is also consistent with the meaning of "one or more", "at least one" and "one or more than one".

As used herein, the word "antimicrobial" means the destruction and/or inactivation of a pathogenic microorganism/microbe.

The use of the word "antiviral" and "virucidal" may be used interchangeably herein to mean the destruction and/or inactivation of a virus.

The use of the word "antibacterial" and "bactericidal" may be used interchangeably herein to mean the destruction and/or inactivation of bacteria.

The use of the word "antifungal" and "fungicidal" may be used interchangeably herein to mean the destruction and/or inactivation of a fungus.

As used herein, the words "comprising" (and grammatical variations thereof, such as "comprise" and "comprises"), "having" (and grammatical variations thereof, such as "have" and "has"), "including" (and grammatical variations thereof, such as "includes" and "include"), or "containing" (and grammatical variations thereof, such as "contains" and "contain"), are inclusive or open-ended and do not exclude additional, unrequited elements or method steps.

The terms "attenuate", "inhibit", "prevent", "treat", and grammatical variations thereof, as used herein, refer to a measurable decrease in a given parameter or event.

The term "pathogen", as used herein, refers to an organism capable of causing a disease or disorder in a host including, but not limited to, bacteria, viruses, protozoa, fungi and parasites.

The term "Minimum Inhibitory Concentration" or "MIC", as used herein, refers to the lowest concentration of an antimicrobial compound/agent that reduces the viability of the initial microbial inoculum by ≥99.9%.

The term "antimicrobial resistance" or "antimicrobial resistant", as used herein, refers to a pathogen that is resistant to one or more antimicrobial agent.

The term "multidrug resistant" or "MDR", as used herein, refers to a pathogen that is resistant to more than one antimicrobial agent, drug, or medicament.

The term "complex bond" as used herein, also known as an acid-base Lewis interaction, a coordinate bond or chelated bond or co-ordinate covalent bond, forms a coordination compound in which a silver ion is attached by coordinate covalent bonds to the GO. The bonding in a complex or chelate bond occurs because the oxygen groups of the GO have at least 2 pairs of unshared electrons; and both the electrons involved in the bonding comes from this ligand These pairs of unshared electrons are regions of negative electrical charge to which are attracted the silver cations. If only 2 pairs of unshared electrons form a complex with silver, this is known as a bidentate arrangement. If 3 pairs of unshared electrons form a complex with silver, this is known as a tridentate arrangement.

It is contemplated that any embodiment discussed herein can be implemented with respect to any method of composition of the invention, and vice versa. Furthermore, compositions of the invention can be used to achieve the methods of the invention.

Preparation of Graphene Oxide/Silver Cation Nanocomposites

Graphene Oxide (GO) is a two-dimensional form of carbonaceous material that has oxygen-containing groups added to its edges and basal planes including epoxide, carboxyl and hydroxyl groups. GO is known to have a large surface area, and exhibits no corrosive characteristics. GO can be synthesized by standard techniques known in the art, for example, Staudenmaier, Hofmann, Brodie, Hummers, and electrochemical exfoliation, which are methods that involve mechanical or thermal exfoliation, chemical vapour deposition (CVD), and epitaxial growth.

According to certain embodiments, the GO can be synthesized by any of the standard methods known in the art. In certain embodiments, the GO can be synthesized by electrochemical exfoliation. In further embodiments, the GO can be synthesized by the Hummers' method.

According to further embodiments, the GO can be synthesized by a modified version of the Hummers' method. In certain embodiments, the GO is synthesized by a modified version of the Hummers' method in which phosphoric acid is eliminated from the process steps. It has unexpectedly been found that by eliminating the use of phosphoric acid from the synthetic process, fewer chemicals are required and synthesis is more efficient, and involving fewer steps.

In preferred embodiments, the GO is synthesized to maximize the available surface area for attachment of ionic silver. According to such embodiments, the method is adapted for the synthesis of smaller graphene flakes to produce GO having increased surface area. In certain embodiments, for example, the GO flake size is reduced through sonication. In certain embodiments, the graphene flakes have a particle size ranging from 500 nm to 5 μm. In further embodiments, the graphene flakes have a particle size ranging from 750 nm to 4 μm. In additional embodiments, the graphene flakes have a particle size ranging from 1 to 3 μm.

In various embodiments, the GO has an oxygen content between 5 to 40%. In further embodiments, the GO has an oxygen content of between 10 to 35%. In additional embodiments, the GO has an oxygen content between 15 to 25%. In further embodiments, the GO has an oxygen content of between 20 to 25%. In other embodiments, the GO has an oxygen content between 20 to 35%. In additional embodiments, the GO has an oxygen content between 28 to 35%.

In various embodiments, the GO has between 1 to 10 layers with a d-spacing that ranges between 0.3 nm to 1 nm. In certain embodiments, the GO has between 1 to 10 layers with a d-spacing that ranges between 0.3 to 0.8 nm. In further embodiments, the GO has between 1 to 10 layers with d-spacing that is at least about 0.8 nm. In additional embodiments, the GO has between 1 to 10 layers with d-spacing that is at least about 0.4 nm.

In certain embodiments, the GO has at least 3 layers. In further embodiments, the GO has at least 4 layers. In additional embodiments, the GO has at least 5 layers. In other embodiments, the GO has at least 7 layers.

Silver nanoparticles (AgNPs) have been widely studied as an antimicrobial agent, however, the effectiveness of AgNPs for inactivating various types of bacteria and viruses is limited by the ability of AgNPs to release silver ions. The release rate of $Ag^+$ from AgNPs to interact directly with phosphorus- or sulphur-containing biomolecules, including DNA, RNA, and proteins, affects the antimicrobial efficacy of AgNPs. In particular, the size, shape, and concentration of AgNPs have been identified as limiting factors that affect their antimicrobial capabilities.

Accordingly, various embodiments described herein relate to the attachment of silver cations ($Ag^+$) to GO. In certain embodiments, the GO comprises between 3-25% w/w of silver in its cationic form. In other embodiments, the concentration of cationic silver bonded to GO is between 5-15% w/w. In further embodiments, the concentration of cationic silver bonded to GO is between 10-20% w/w. According to further embodiments, the concentration of cationic silver bonded to GO is between 3-10% w/w. In other embodiments, the concentration of cationic silver bonded to GO is between 4-8% w/w.

According to further embodiments the GO-$Ag^+$ nanocomposite also includes colloidal silver, i.e., AgNPs. In such embodiments, the GO-$Ag^+$/AgNP nanocomposite can comprise these two forms of silver in ratios of $Ag^+$:AgNP of 500:1, 400:1, 300:1, 200:1, 100:1, 90:1, 80:1, 70:1, 60:1, 50:1, 40:1, 30:1, 20:1, 10:1, and 5:1. In certain embodiments, the ratio of $Ag^+$:AgNP bonded to the GO nanocomposite is 50:1. According to further embodiments, the ratio of $Ag^+$:AgNP bonded to the GO nanocomposite is 40:1. According to other embodiments, the ratio of $Ag^+$:AgNP bonded to the GO nanocomposite is 20:1. According to certain embodiments, the ratio of $Ag^+$:AgNP bonded to the GO nanocomposite is 15:1. In further embodiments, the ratio of $Ag^+$:AgNP bonded to the GO nanocomposite is 10:1. According to certain embodiments, the ratio of $Ag^+$:AgNP bonded to the GO nanocomposite is 11:1. In further embodiments, the ratio of $Ag^+$:AgNP bonded to the GO nanocomposite is between 10:1 and 15:1.

FIG. 1 illustrates the non-limiting reaction of the adhesion of ionic $Ag^+$ and AgNPs to the GO contemplated herein.

It is further contemplated that the GO-$Ag^+$ nanocomposite described herein may also include additional metals. Illustrative but non-limiting nanocomposites described herein comprise GO-$Ag^+$ nanocomposite and one or more other metals. Illustrative other metals include, but are not limited to copper (e.g., copper ion, copper nanoparticles), gold (gold ion, gold nanoparticles), and zinc (zinc ion, zinc nanoparticles).

In certain embodiments, the GO-$Ag^+$ nanocomposite described herein are mixed with additives such as cations and nanomaterials or a combination of these. Cations include but not limited to $Ag^+$, $Cu^{2+}$, $Zn^{2+}$. And metallic nanomaterials including but not limited to Ag, Cu, Zn. In further embodiments, these additives are chemically bonded to GO and in some cases physically adsorbed onto the GO thereto.

In accordance with one non-limiting aspect of the present invention, an antimicrobial nanocomposite is produced by a method comprising:

(a) synthesizing graphene oxide (GO), comprising the steps of:
  (i) mixing graphite powder with a 98% sulfuric acid solution at a volume-to-mass ratio of about 30 mL:1 g of the sulfuric acid solution to the graphite powder to from a suspension;
  (ii) sonicating the suspension for 30 minutes at three, 6-hour intervals, at 50° C.;
  (iii) transferring the suspension to an ice-water bath and gradually adding potassium permanganate to the suspension, wherein the mass ratio of said potassium permanganate to graphite powder is about 4:1;
  (iv) stirring the mixture for up to 12 hours at 35° C. with intermittent sonication for 15 to 30 minutes after 8 hours;
  (v) reducing the temperature of the mixture to below 5° C. in an ice-bath and adding distilled water having a temperature of between 2-5° C. to the mixture, wherein the volume to mass ratio of the water to graphite being about 100 mL:1 g;
  (vi) adding 30% hydrogen peroxide dropwise to the mixture until the mixture changes color from dark brown to yellow;
  (vii) sonicating the mixture for 30 minutes to accelerate the separation of GO nanosheets; and
  (viii) purifying the GO nanosheets by washing 3 times with 1 M hydrochloric solution followed by washing 3 times with a mixture of water and ethanol (8:2 v/v), wherein the mixture is sonicated for 30 minutes between each washing and the pH of the mixture adjusted to between 3 and 4 by the addition of 1 M potassium hydroxide solution; and (b) fixing silver cations to the GO nanosheets, comprising the steps of:
  (i) sonicating the GO nanosheets in deionized water for 30 minutes, wherein the volume-to-mass ratio of the GO nanosheets to water is about 0.1 g:30 mL, to form a suspension, and adjusting the pH of the suspension to 10 using a 0.1 M sodium hydroxide solution;
  (ii) adding a 10 M silver nitrate solution to the suspension, wherein the volume to mass ratio of the silver nitrate solution to GO nanosheets being about 0.1 g:2 mL;
  (iii) adding deionized water to the suspension and stirring for 20 hours at 60° C. to reduce the viscosity of the solution, wherein the volume to mass ratio of the deionized water to GO nanosheets being about 0.1 g:20 mL; and
  (iv) centrifuge-washing the suspension in deionized water 3 times to collect the graphene oxide-silver cation nanocomposite.

Without being limited to any particular theory, it is believed that GO silver cation nanocomposites are formed in part by a first silver cation monolayer being deposited and strongly bonded to the GO sheet, with successive layers of silver cations being weakly bonded primarily through physisorption.

Antimicrobial Activity

In various embodiments, the GO-$Ag^+$ nanocomposites described herein, and/or compositions or formulations comprising these nanocomposites, exhibit antimicrobial activity against a spectrum of microbial targets. In particular, it was unexpectedly found that the GO-Ag⁺ nanocomposites described herein exhibit a Minimum Inhibitory Concentration (MIC) of <1 µg/mL against a spectrum of microbial targets. The unexpectedly low MIC values exhibited across the spectrum suggest that the GO-Ag⁺ nanocomposites are effective antimicrobial agents with minimal risk of toxicity for animals and humans.

According to certain embodiments, the GO-Ag⁺ nanocomposites described herein exhibit an MIC of <1 µg/mL against microbial pathogens. In further embodiments, the GO-Ag⁺ nanocomposites described herein exhibit an MIC of <0.5 µg/mL against microbial pathogens. In other embodiments, the GO-Ag⁺ nanocomposites described herein exhibit an MIC of <0.25 µg/mL against microbial pathogens. In further embodiments, the GO-Ag⁺ nanocomposites described herein exhibit an MIC of <0.125 µg/mL against microbial pathogens. In other embodiments, the GO-Ag⁺ nanocomposites described herein exhibit an MIC of <0.0625 µg/mL against microbial pathogens. In further embodiments, the GO-Ag⁺ nanocomposites described herein exhibit an MIC of <0.031 µg/mL against microbial pathogens. In other embodiments, the GO-Ag⁺ nanocomposites described herein exhibit an MIC of <0.0156 µg/mL against microbial pathogens. In further embodiments, the GO-Ag⁺ nanocomposites described herein exhibit an MIC of <0.008 µg/mL against microbial pathogens.

In certain embodiments, the GO-Ag⁺ nanocomposites described herein exhibit an antimicrobial efficacy against viral, bacterial, and/or fungal pathogens. In further embodiments, the GO-Ag⁺ nanocomposites described herein, and/or compositions or formulations comprising these nanocomposites, exhibit virucidal and/or antiviral effect against viral targets, including but not limited to, enveloped viruses such as herpesviruses, poxviruses, hepadnaviruses, asfarviridae, flavivirus, alphavirus, togavirus, coronavirus, hepatitis D, orthomyxovirus, paramyxovirus, rhabdovirus, bunyavirus, filovirus, retroviruses. According to further embodiments, the GO-Ag⁺ nanocomposite compositions exhibit virucidal and/or antiviral effect against viral pathogens that include, for example, viruses from the family Adenoviradae; Arenaviridae (for example, Ippy virus and Lassa virus); Birnaviridae; Bunyaviridae; Caliciviridae; Coronaviridae; Filoviridae; Flaviviridae (for example, yellow fever virus, dengue fever virus and hepatitis C virus); Hepadnaviradae (for example, hepatitis B virus); Herpesviradae (for example, human herpes simplex virus 1); Orthomyxoviridae (for example, influenza virus A, B and C); Paramyxoviridae (for example, mumps virus, measles virus and respiratory syncytial virus); Picornaviridae (for example, poliovirus and hepatitis A virus); Poxviridae; Reoviridae; Retroviradae (for example, BLV-HTLV retrovirus, HIV-1, HIV-2, bovine immunodeficiency virus and feline immunodeficiency virus); Rhabodoviridae (for example, rabies virus), and Togaviridae (for example, rubella virus). Non-limiting examples of relevant pathogenic viruses include, but are not limited to, various strains of the influenza virus, cytomegalovirus, various strains of respiratory syncytial virus (including human respiratory syncytial virus and specific animal strains), various strains of parainfluenza virus (including human parainfluenza virus and specific animal strains), coronavirus (including human coronavirus, SARS coronavirus, MERS coronavirus, and Covid-19 coronavirus), rhinovirus (including human rhinovirus), enterovirus (including human enterovirus), adenovirus (including human adenovirus), bocavirus (including human bocavirus), metapneumovirus (including human metapneumovirus), dengue virus, various hepatitis viruses, human immunodeficiency virus (HIV), West Nile virus, rabies virus, human papilloma virus (HPV), Epstein Barr virus (EBV) and polyoma virus. In certain embodiments of the invention, the GO-Ag⁺ nanocomposites exhibit virucidal and/or antiviral effect against influenza virus, a flavivirus (such as dengue fever virus or yellow fever virus), a parainfluenza virus, human metapneumovirus, respiratory syncytial virus, coronavirus (such as Covid-19 coronavirus, SARS coronavirus, MERS coronavirus), a rhinovirus or an adenovirus.

In further embodiments, the GO-Ag⁺ nanocomposites described herein, and/or compositions or formulations comprising these nanocomposites, exhibit antibacterial effect against bacterial pathogens. According to certain embodiments, bacterial pathogens include gram positive bacteria. In other embodiments, the bacterial pathogens include gram negative bacteria. Bacterial pathogens include, for example, various species of the *Bacillus, Yersinia, Franscisella, Haemophilus, Streptococcus, Staphylococcus, Pseudomonas, Mycobacterium*, and *Burkholderia* genus of bacteria. Non-limiting examples of relevant pathogenic bacterial species include, but are not limited to, *Bacillus anthracis, Yersinia pestis, Francisella tularensis, Streptococcus pnemoniae, Staphylococcus aureus, Pseudomonas aeruginosa, Burkholderia cepacia, Corynebacterium diphtherias, Legionella pneumophila, Mycoplasma pneumoniae, Chlamydophila pneumoniae, Mycobacterium tuberculosis, Moraxella catarrhalis, Haemophilus influenzae, Klebsiella pneumoniae, Escherichia coli, Coxiella burnetii, Clostridia* spp. and *Shigella* spp.

In certain embodiments, the GO-Ag⁺ nanocomposites described herein, and/or compositions or formulations comprising these nanocomposites, exhibit antifungal effect against fungal pathogens. Fungal pathogens include, for example, *Histoplasma capsulatum, Coccidiodes immitis, Blastomyces dermatitidis, Cryptococcus neoformans, Aspergillus fumigatus, Candida albicans* and *Pneumocystis carinii*.

In further embodiments, the GO-Ag⁺ nanocomposites described herein exhibit an antimicrobial efficacy against antimicrobial resistant (AMR) and/or multidrug resistant (MDR) microbial pathogens. In certain embodiments, the AMR and/or MDR pathogens include *Pseudomonas aeruginosa, Escherichia coli, Klebsiella pneumoniae, Serratia marcescens, Acinetobacter baumanii, Stenotrophomonas maltophilia, Streptococcus pneumonia, Staphylococcus aureus, Candida auris, influenza virus*, Extended Spectrum Beta-lactamase (ESBL) *Escherichia coli*, ESBL *Klebsiella pneumoniae*, Carbapenem Resistant Organisms (CRO) *Enterobacter* spp., Penicillin-resistant *Streptococcus pneumonia*, CA-MRSA, HA-MRSA, and *Acinetobacter baumanii* complex. In other embodiments, the GO-Ag⁺ nanocomposites described herein exhibit an antimicrobial efficacy against antimicrobial resistant (AMR) and/or multidrug resistant (MDR) microbial pathogens known as the ESKAPE pathogens. According to such embodiments, the GO-Ag⁺ nanocomposites described herein exhibit an antimicrobial efficacy against any one or more of *Enterococcus faecium, Staphylococcus aureus, Klebsiella pneumoniae, Acinetobacter baumannii, Pseudomonas aeruginosa*, and *Enterobacter* spp.

Antimicrobial Formulations

The present invention provides for antimicrobial formulations comprising the GO-Ag⁺ nanocomposite. The formulations can be formulated for application by a variety of methods. For example, the formulations can be formulated as a powder, spray, gel, foam, films or coating for application to a substrate. In certain embodiments, as would be within the knowledge of a skilled technician, the formulations can include one or more suitable agents, carriers, diluents and/or dispersents. If desired, other active ingredients may be included in the formulations, for example, additional anti-microbial agents, or the like.

According to various embodiments, the GO-Ag$^+$ nano-composite formulations described herein can be provided in a solution and/or suspension, and/or dispersion, and/or emulsion to facilitate the application of the GO-Ag$^+$ nano-composites to a substrate surface. For example, the GO-Ag$^+$ nanocomposites described herein are formulated as an aque-ous suspension by suspending the GO-Ag$^+$ nanocomposite in an industry accepted solvent, carrier, and/or diluent. In certain embodiments, the formulation comprises the GO-Ag$^+$ nanocomposites described herein and ethanol; deion-ized water; both ethanol and deionized water; isopropyl alcohol; isopropyl alcohol and deionized water; isopropyl alcohol, ethanol and deionized water; isopropyl alcohol, hydrogen peroxide, deionized water; hydrogen peroxide, ethanol, isopropyl alcohol and water, or any combination thereof. According to certain embodiments, the antimicro-bial formulations described herein have a concentration of GO-Ag$^+$ nanocomposites of between about 40 mg/L to 5 g/L. In other embodiments, the formulations comprise GO-Ag$^+$ nanocomposites at a concentration of between about 2 to 20 g/L. In further embodiments, the formulations com-prise GO-Ag$^+$ nanocomposites at a concentration of between about 3 to 5 g/L.

In certain embodiments, the antimicrobial formulations may be formulated as a dispersible powder or granules, which can subsequently be used to prepare an aqueous suspension by the addition of a suitable solvent, carrier, and/or diluent, for example, water. Such dispersible powders or granules provide the GO-Ag$^+$ nanocomposite in admix-ture with one or more dispersing or wetting agents and/or suspending agents. Suitable dispersing or wetting agents and suspending agents are exemplified by those already men-tioned above. Additional additives, for example, colouring agents and/or fragrances can also be included in these formulations.

According to certain embodiments, the formulations can be prepared for application by spin coating, dip coating, dip-coat bath, spray coating, solvent evaporation. In such embodiments, the GO-Ag$^+$ nanocomposite coating is fixed by air drying, heat drying, thermal drying, sun drying or vacuum drying or drying under ambient conditions or a combination of these techniques. According to certain embodiments, the GO-Ag$^+$ nanocomposite is coated to the substrate surface at a thickness that ranges from about 5 nm to about 5 μm. In other embodiments, the GO-Ag$^+$ nano-composite is coated to the substrate surface at a thickness that ranges from about 100 nm to about 3 μm. In further embodiments, the GO-Ag$^+$ nanocomposite is coated to the substrate surface at a thickness that ranges from about 200 nm to about 2 μm. In additional embodiments, the GO-Ag$^+$ nanocomposite is coated to the substrate surface at a thick-ness that ranges from about 300 nm to about 1.5 μm. In other embodiments, the GO-Ag$^+$ nanocomposite is coated to the substrate surface at a thickness that ranges from about 500 nm to about 1.0 μm.

Once applied to a substrate surface, the formulations of the GO-Ag$^+$ nanocomposites described herein are stable, maintaining the ability to kill (or otherwise inactivate) at least between 75-100% of pathogens on contact with the formulation post-application to the treated surface. In a further aspect, such formulations are stable for at least 3 to 6 weeks post-application to kill (or otherwise inactivate) at least between 90-100% of pathogens on contact with the formulation on the treated surface. In other embodiments, the antimicrobial effect of the formulations of the GO-Ag$^+$ nanocomposites described herein persists for up to 3 months. According to further embodiments, the antimicro-bial effect of the formulations of the GO-Ag$^+$ nanocompos-ites described herein persists for up to 2 months. In addi-tional embodiments, the antimicrobial effect of the formulations of the GO-Ag$^+$ nanocomposites described herein persists for up to 1 month. According to various embodiments, the formulations described herein confer highly antimicrobial properties to a treated surface that remain stable for prolonged periods.

In several embodiments, the above-referenced formulary components can be used in various, non-limiting combina-tions in order to provide a formulation that is optimized for a particular purpose (e.g., targeting preferentially a particu-lar type (or types) of microorganism, killing or inhibiting at a certain level, etc.). Moreover, in several embodiments, the above-referenced components that make up any given embodiment of the formulation may be recognized by those of skill in the art by commercial or trade names, or chemical nomenclature of formula. Other formulations and methods of preparing antimicrobial formulations are known in the art and are within the capacity of the skilled technician.

Methods and Uses

The GO-Ag$^+$ nanocomposites described herein, and/or compositions or formulations comprising these nanocom-posites, are useful as broad-spectrum antimicrobial includ-ing antiviral, antibacterial, and/or antifungal agent in a wide variety of applications. For example, the GO-Ag$^+$ nanocom-posites can be used to disinfect a variety of materials including equipment, textiles, enclosure walls, countertop surfaces, or any high touchpoint surface of a metal, plastic, stone, and/or wood. The GO-Ag$^+$ nanocomposites can fur-ther be used as a surface coating to convey a broad-spectrum antimicrobial, antiviral, antibacterial, and/or antifungal properties to a variety of materials and articles of manufac-ture including, for example, and without limitation, PPE, face masks, counters, door handles, walls, filters in air filtration (HVAC) systems, and other airflow membranes and filters, to reduce or eliminate the activity of the micro-bial pathogens.

The disinfectant formulations of the present invention may be applied onto a surface to be disinfected (i.e. cleaned) by means of a variety of spraying techniques. In an embodi-ment, the disinfectant formulations of the present invention are applied using a spray nozzle, diffuser or mist blower. Alternatively, the disinfectant formulations of the present invention can also be formulated into aerosol formulations. Further means of applying the disinfectant solutions of the present invention are within the capacity of a skilled tech-nician. The disinfectant formulations of the present inven-tion can either be applied directly or can be diluted prior to application.

In certain embodiments, the GO-Ag$^+$ nanocomposites described herein are particularly useful as virucidal and/or antiviral agents against viral pathogens such as enveloped viruses. According to further embodiments, the GO-Ag$^+$ nanocomposites described herein are useful as virucidal and/or antiviral agents against coronavirus. In further

15 embodiments, the GO-Ag⁺ nanocomposites described herein are useful as virucidal and/or antiviral agents against SARS-CoV-2 virus.

In various embodiments, the GO-Ag⁺ nanocomposites described herein can be used directly, provided in a composition/formulation, or adhered to the surface of an article of manufacture. Thus, for example, the GO-Ag⁺ nanocomposites described herein can be provided for direct use in a solution and/or suspension, and/or dispersion, and/or emulsion. In certain embodiments, the GO-Ag⁺ nanocomposites described herein can be adhered or coated (e.g., adsorbed or conjugated) to the surface of an article of manufacture to confer antimicrobial, antiviral, antibacterial, and/or antifungal properties to that article of manufacture. Thus, for example, the GO-Ag⁺ nanocomposites described herein can be adhered to the surface of high touchpoint surfaces of metal, plastic, stone, wood.

In addition to reducing microbial transmission through transfer from high touchpoint surfaces, the GO-Ag⁺ nanocomposites described herein can further be adhered to certain surfaces to reduce microbial transmission through aerosols in the air. For example, the GO-Ag⁺ nanocomposites described herein can be adhered to face masks, protective clothing, respirators, and other PPE, filters in HVAC systems and other airflow membranes and filters, to trap and reduce the microbial pathogen activity or destroy the microbial pathogen. In certain embodiments, the GO-Ag⁺ nanocomposites described herein can be adhered or coated to the surface of PPE, face masks, counters, door handles, walls, filters in air filtration (HVAC) systems, and other airflow membranes and filters. In certain embodiments, the GO-Ag⁺ nanocomposites described herein can be used to enhance the filtration efficiency of a substrate, such as a medical mask, PPE, airflow membranes and filters. In certain embodiments, the GO-Ag⁺ nanocomposites described herein can increase the bacterial and viral filtration efficiency of face masks and filters in air filtration (HVAC) systems. According to further embodiments, the GO-Ag⁺ nanocomposites described herein can be used to enhance the filtration efficiency of water filtration membranes including but not limited to reverse osmosis, dialysis and ion selective membranes and filters including filter papers, cloths, substrate filter beds. According to embodiments, the application of the GO-Ag⁺ nanocomposites described herein enhances the filtration efficiency of a treated substrate by at least 85%, 90%, 95%, 97%, 98%, or 99% more than the uncoated substrate.

In various embodiments, the GO-Ag⁺ nanocomposites described herein, and/or compositions or formulations comprising these nanocomposites are used to kill, trap, immobilize, and/or to otherwise inactivate any of a wide variety of pathogen targets, and/or to prevent pathogen transmission and diseases related thereto in animals and humans.

To gain a better understanding of the invention described herein, the following examples are set forth. It will be understood that these examples are intended to describe illustrative embodiments of the invention and are not intended to limit the scope of the invention in any way.

EXAMPLES

Example 1: Preparation of Graphene—Silver Cation Nanocomposite

GO-Ag⁺ nancomposite was prepared according to the following method based on 1 g graphite powder.
Synthesis of GO
1 g graphite powder was soaked in 30 mL H₂SO₄ (98%) solution under the fume hood in an Erlenmeyer under stirring at 50° C. and 300 rpm for 18 h. The suspension was sonicated 3 times every 6 h using a bath sonicator for 30 min. Then, 4 g KMnO₄ was added gradually to the previous mixture. An ice/water bath was used to decrease the temperature of the mixture during the exothermic oxidation reactions. The mixture was kept under continuous stirring for up to 12 h at 35° C. Bath sonication (15-30 min) was used 3 times after 8 h of stirring in this stage. Next, 100 mL of cold distilled water (2-5° C.) was added to the previous mixture. In this stage, the temperature of the mixture was kept below 5° C. using an ice-bath. Then, H₂O₂ (30%) was added drop-by-drop to the diluted mixture until the color of the mixture changed from dark brown to yellow. Before purification, 30 min bath sonication of the mixture was used to accelerate the separation of exfoliated GO nanosheets from each other. The final suspension was washed 3 times with HCl (1 M) and three times with a mixture of water/ethanol (8:2 v/v). Bath sonication (30 min) was used between the purification steps to accelerate the removal of impurities intercalated between the GO layers. pH of the sample was adjusted between 3-4 during the centrifuging by 1 M KOH solution for better sedimentation. The final GO nanosheets were dispersed in distilled water and stored for the next usages.
Silver (Ag⁺) Doped GO Synthesis
Graphene oxide (GO) nanosheets as the platform for cationic silver were synthesized. To synthesize Ag doped GO nanosheets, 1 g dried pristine GO powder was dispersed in 100 mL DI water in a 250 mL Erlenmeyer flask using a bath sonicator for 30 min. The pH of the GO suspension was adjusted at 10 using NaOH solution (0.1 M). Then, 2 mL of the AgNO₃ solutions (10 M) was added to the previous suspension under stirring (400 rpm). The mixture was stirred for 20 h at 60° C. Finally, Ag doped GO nanosheets were collected using a centrifuge (4000 rpm), washed with DI water 3 times, and dried in an oven at ~60° C. overnight.

Example 2: Complex Bonding of Cationic Silver To Go Nanosheets

GO surfaces are known to act like reducing agents. It is possible for some of the Ag⁺ cation to be reduced to metallic Ag(0). This reduction of the cation Ag⁺ could also be associated with simultaneous oxidation of other graphene functionalities (like quinone to hydroquinone). It has also been observed that species with C and O (like phenolic, carbonyl) would oxidise during the process. On the other hand, Ag⁺ could be on the surface in +1 oxidation state or simply coordinated with the oxygen or other functional groups on the GO surface. Where Ag(0) particles are present, they can contact the microorganism (pathogen) and directly act on them by either interfering with the DNA/RNA replication or denaturing other proteins in the cell (ribosome, cell membrane, etc.); alternatively, Ag would come in contact with liquid (surrounding the pathogen), thus oxidizing Ag(0) to Ag(+) and the latter disrupts the cell membrane or denatures the proteins.

To study the silver species attached to the GO-Ag⁺ nanocomposite, and to consider the inclusion of Ag(1)-complexes as well as (Ag(0)) nanoparticles on the GO, peak fitting was performed. X-ray photoelectron spectroscopy (XPS) and Auger Electron Spectroscopy (AES) of one exemplary product according to the present invention (defined in Table 1) was analyzed (see FIGS. 2A, 2B, Table 1).

TABLE 1

| Identified Product Components | | | |
| --- | --- | --- | --- |
| Component | Peak, eV | atm % | wt % |
| C 1s | 284.82 | 71.07 | 49.41 |
| O 1s | 532.42 | 24.46 | 22.65 |
| Ag 3d | 368.02 | 4.47 | 27.94 |

TABLE 2

| Distribution of Ag1-Complex and Clustered Ag(0) | | | |
| --- | --- | --- | --- |
| Component | Peak, eV | FWHM | Composition % |
| Ag(0) [Ag NP cluster] | 368.95 | 1.5 | 7.98 |
| Ag(1) [Ag(1) Complex/Ag2CO3] | 368.02 | 1.34 | 92.02 |

TABLE 3

| Identified Product Components | | | | | |
| --- | --- | --- | --- | --- | --- |
| Element | Position | FWHM | At % conc | Wt % conc | C/O, a/a |
| O 1s | 532.54 | 1.92 | 26.54 | 32.1 | 2.74 |
| C 1s | 286.74 | 3.48 | 72.67 | 65.98 | |
| S 2p | 168.84 | 2.2 | 0.79 | 1.92 | |

Figures 2A, 2B, 2C, 2D:
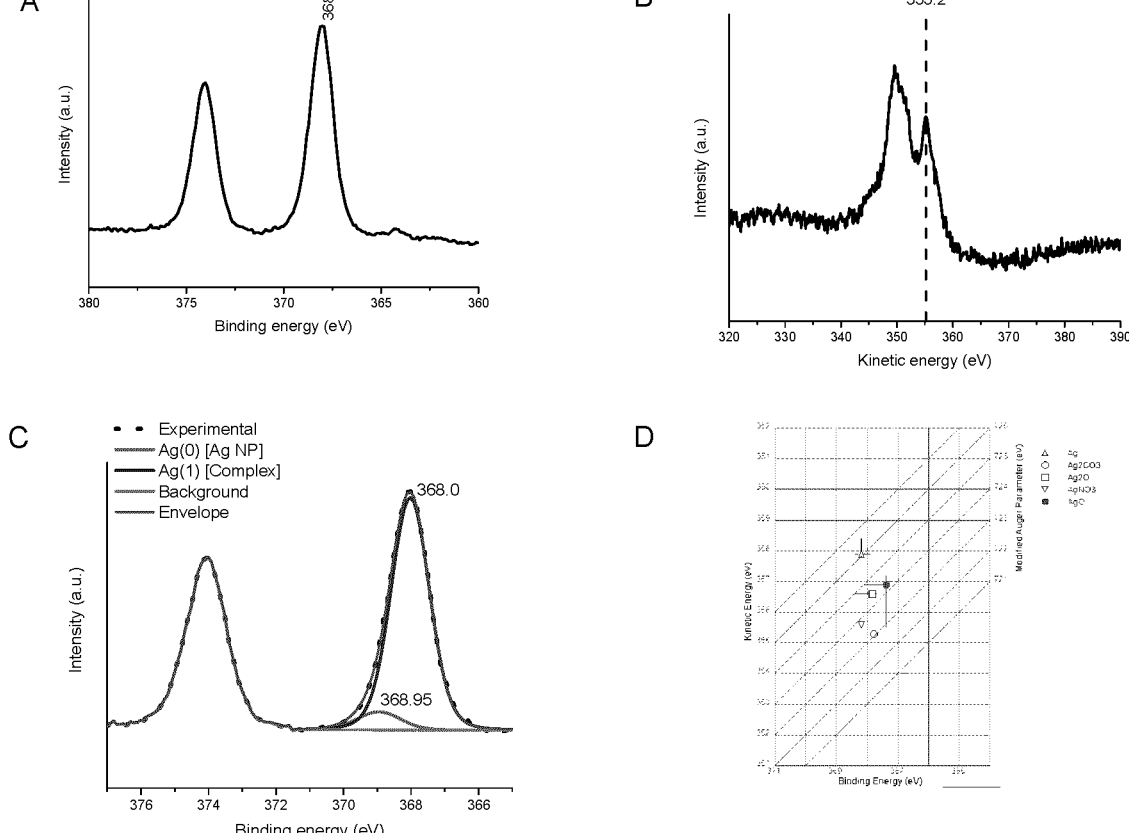
FIGS. 2A to 2D are results of XPS and AES analysis of a sample according to an embodiment of the present invention.
Figure 3:
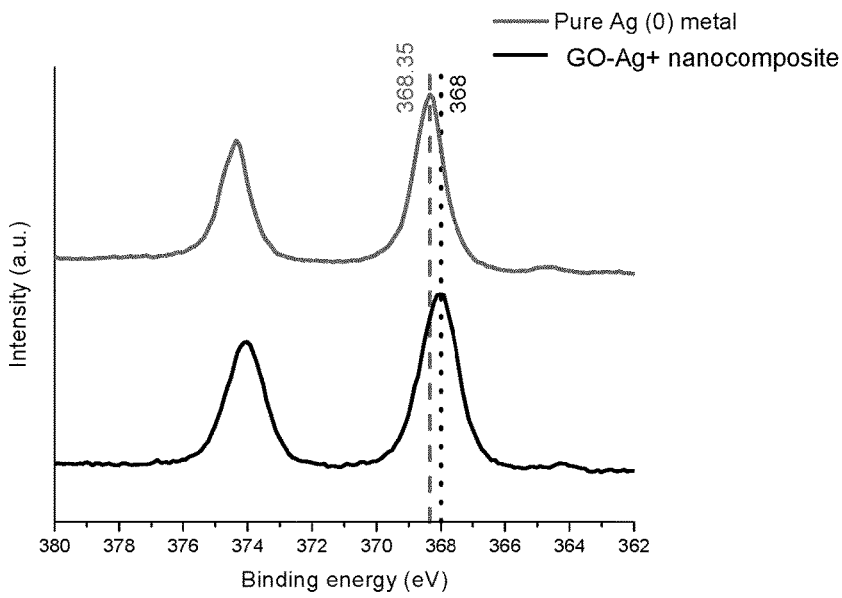
FIG. 3 is a chart showing a comparision of chemical states between silver and silver nano-composites formed.
Figures 4A, 4B:
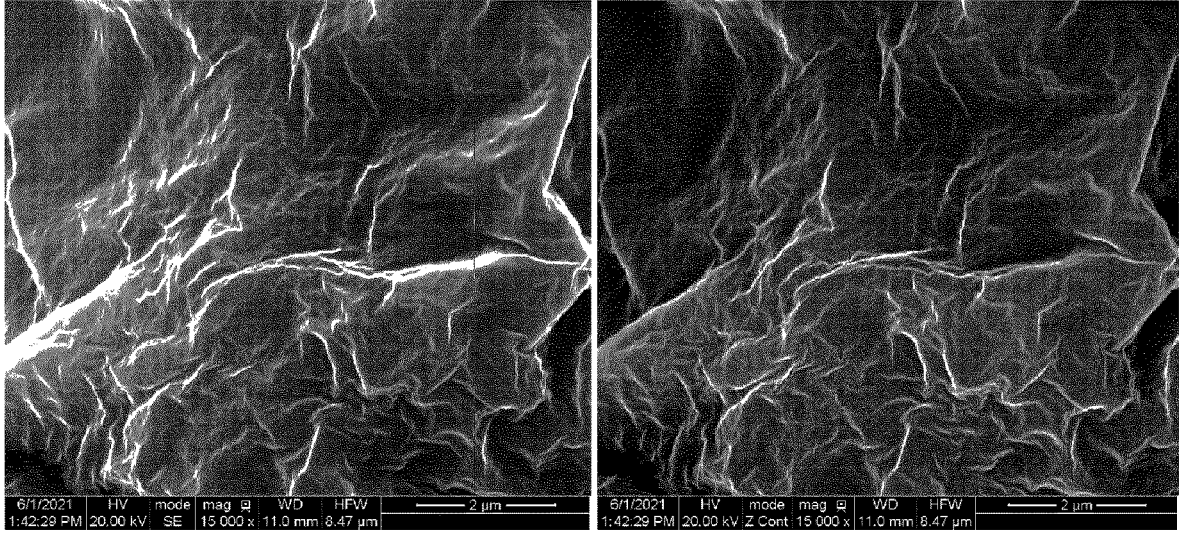
FIGS. 4A to 4F are SEM (SE) and SEM (Backscattered electron image/Z count) images of GO before contact with silver cations.
Figures 4C, 4D:
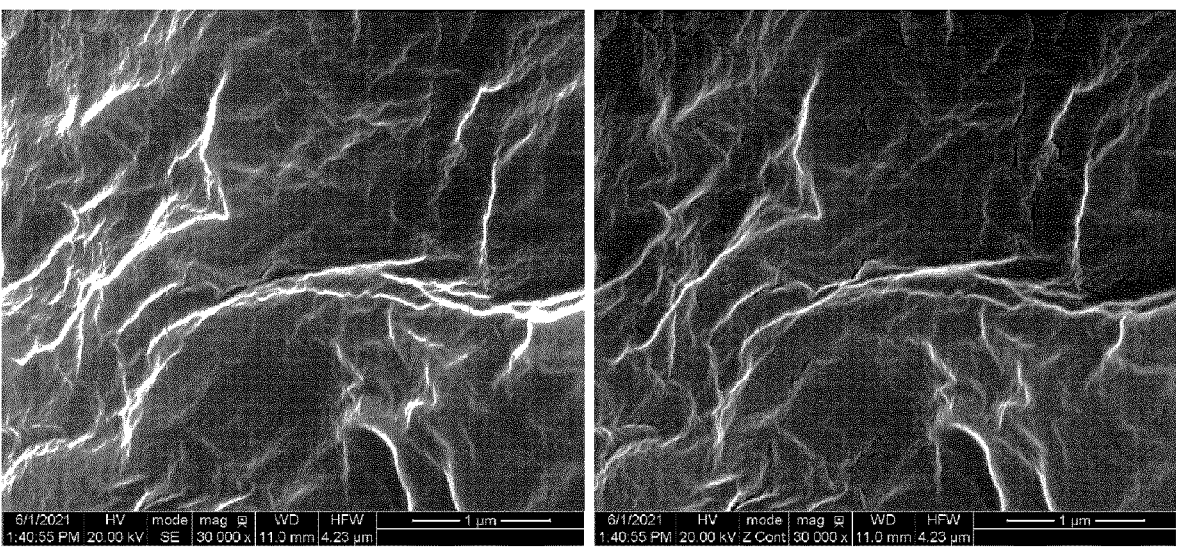
Figures 4E, 4F:
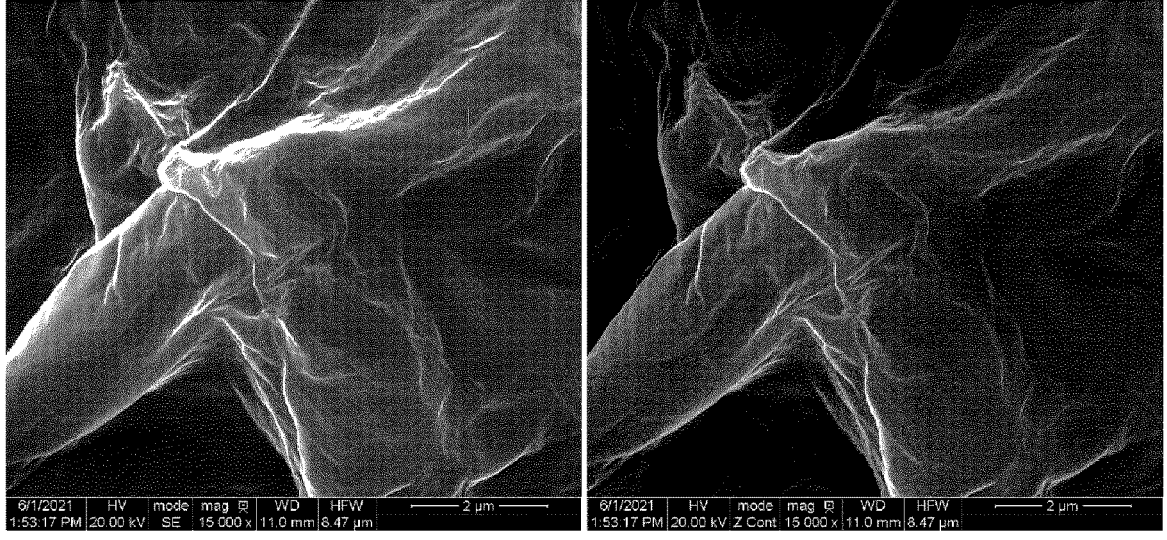

The calculated Auger parameter values for the exemplary product was 723.2 eV, confirming the significant composition is not Ag or Ag2O (see FIGS. 2C, 2D). Peak fitting of the Ag 3d5/2 data (Table 2) indicates that approximately 92% of the silver in the exemplary product is in a Ag(1)-complex form and the remaining 8% could be attributed to clustered Ag(0)-nanoparticle forms. No form of nitrogen was detected, thus confirming the removal of nitrates in the final product. The downward shift of the Ag3d5/2 peak of the exemplary product when compared to Ag(0) clearly indicated the chemical state of the former to be Ag(1) (FIG. 3). Elemental C and O composition of the exemplary product remained similar to the GO elemental composition, except for the addition of approximately 4.5 at % Ag (Tables 1 and 3). This suggests that the Ag(1) ions are complexing with the existing functional groups on the GO. Positively charged Ag(1) ions, which were initially introduced into the system via the addition of AgNO3, are electrostatically attracted towards the negatively charged functional groups with lone pair electrons on the GO surface to form complex bonds such as coordinate covalent bonds (both electrons shared in the bonding are from the functional group on the GO sheet which is the ligand in this case).

Figure 5A:
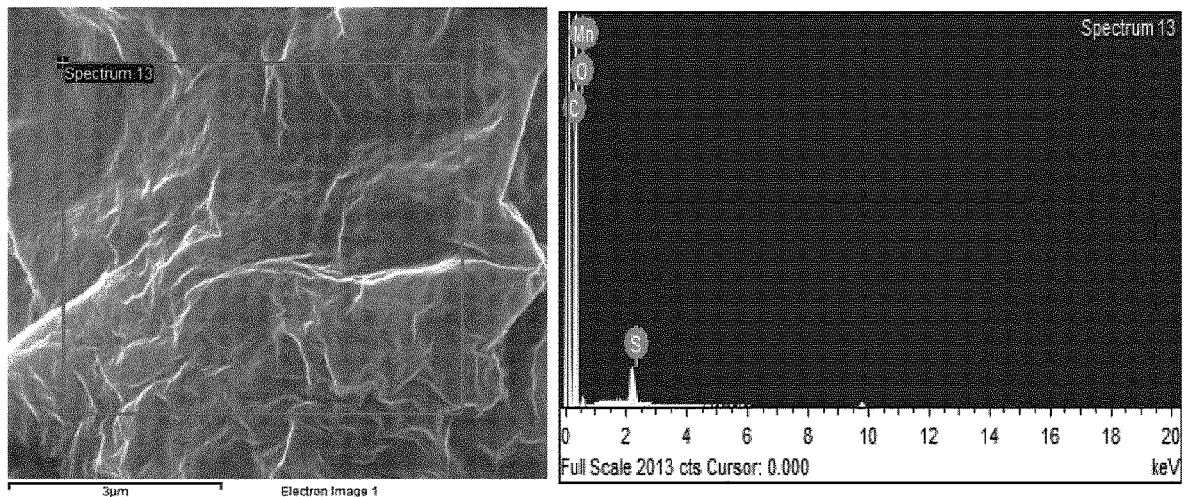
FIGS. 5A to 5C are EDS images and results charts of GO before contact with silver cations.
Figure 5B:
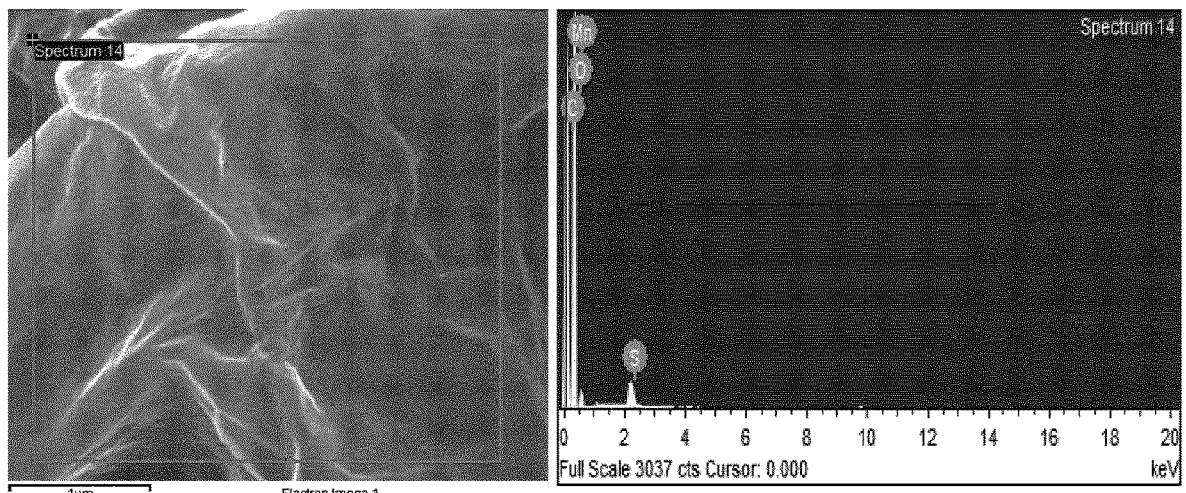
Figure 5C:
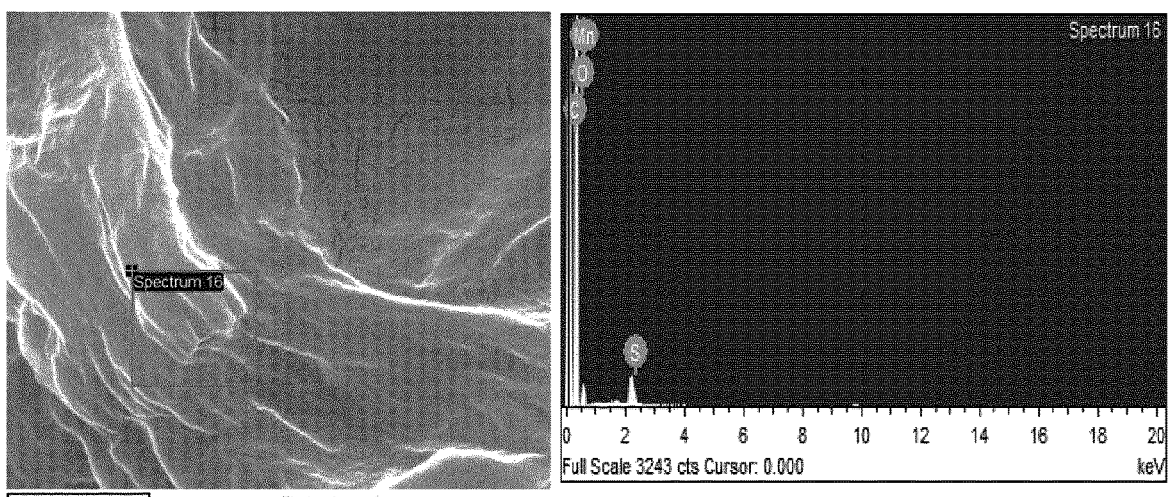
Figures 6A, 6B:
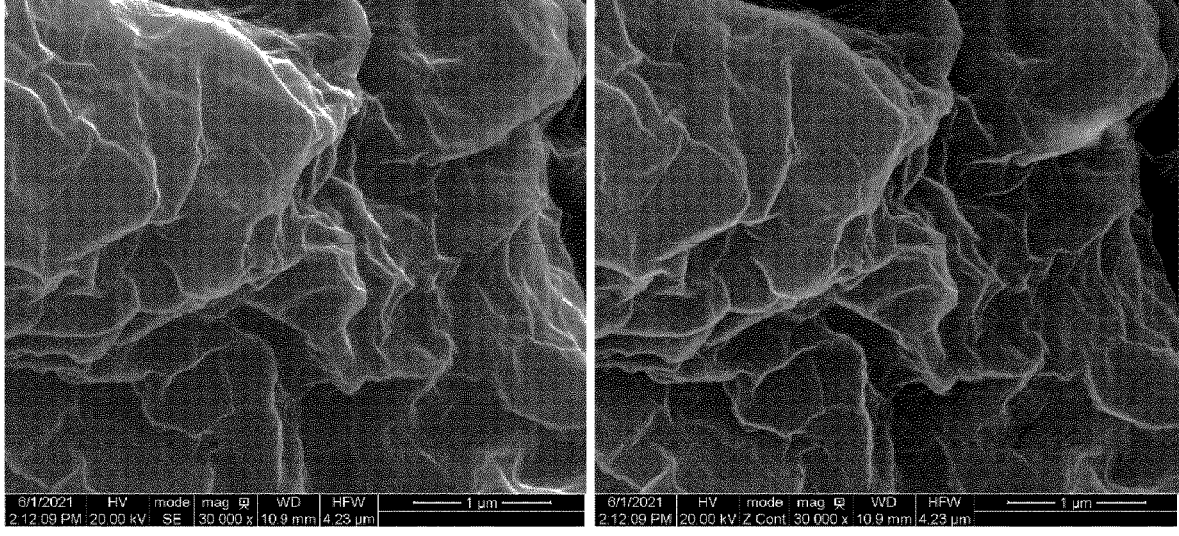
FIGS. 6A to 6F are SEM (SE) and SEM (Z count) images of GO after contact with silver cations but before purification.
Figures 6C, 6D:
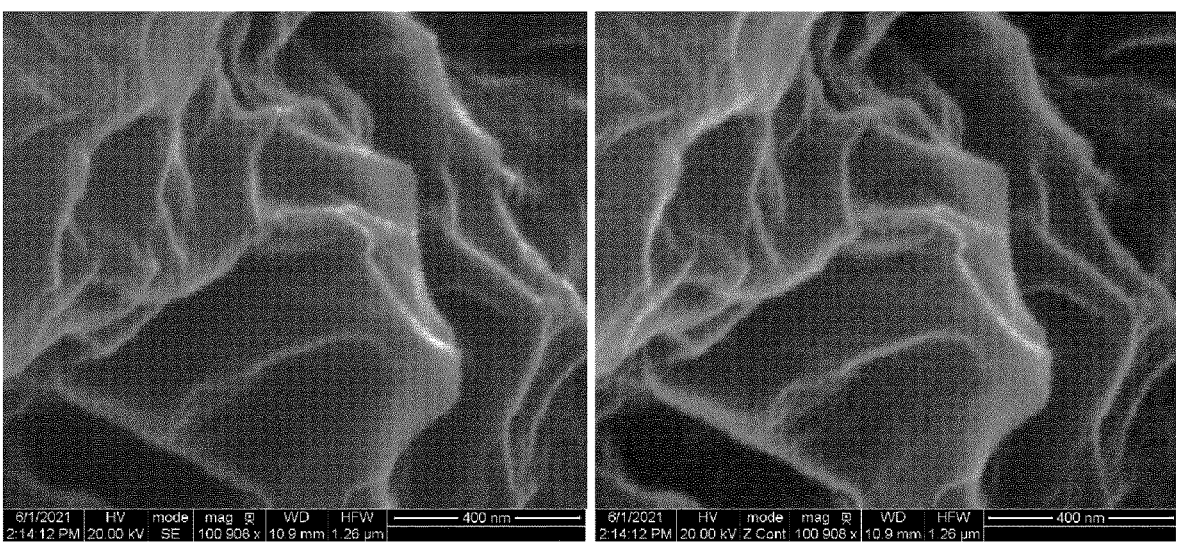
Figures 6E, 6F:
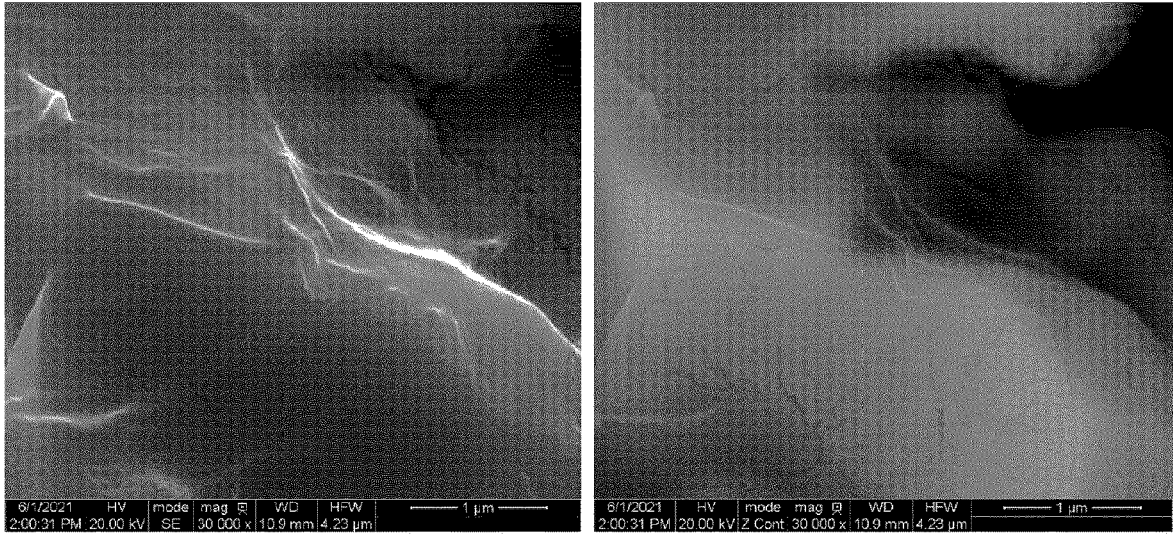
Figure 7A:
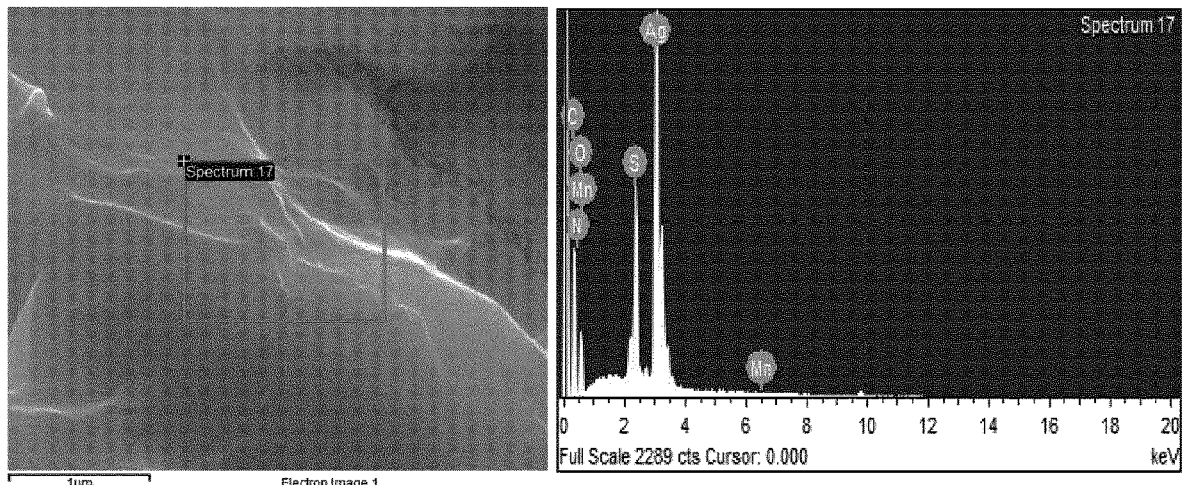
FIGS. 7A and 7B are EDS images and elemental results of GO after contact with silver cations but before purification.
Figure 7B:
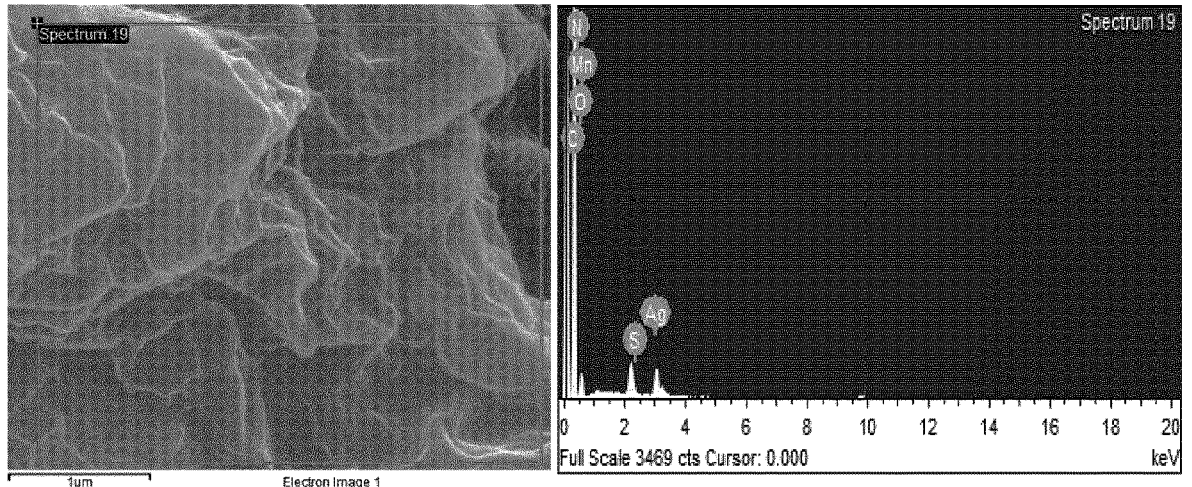
Figures 8A, 8B:
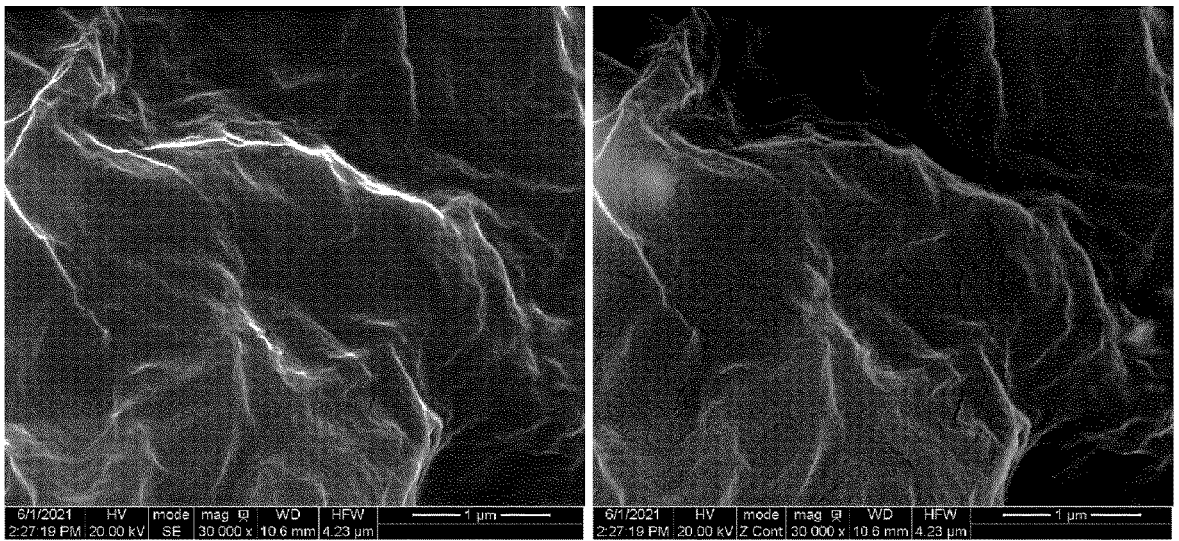
FIGS. 8A to 8D are SEM (SE) and SEM (Z count) images of GO after contact with silver cations and after purification.
Figures 8C, 8D:
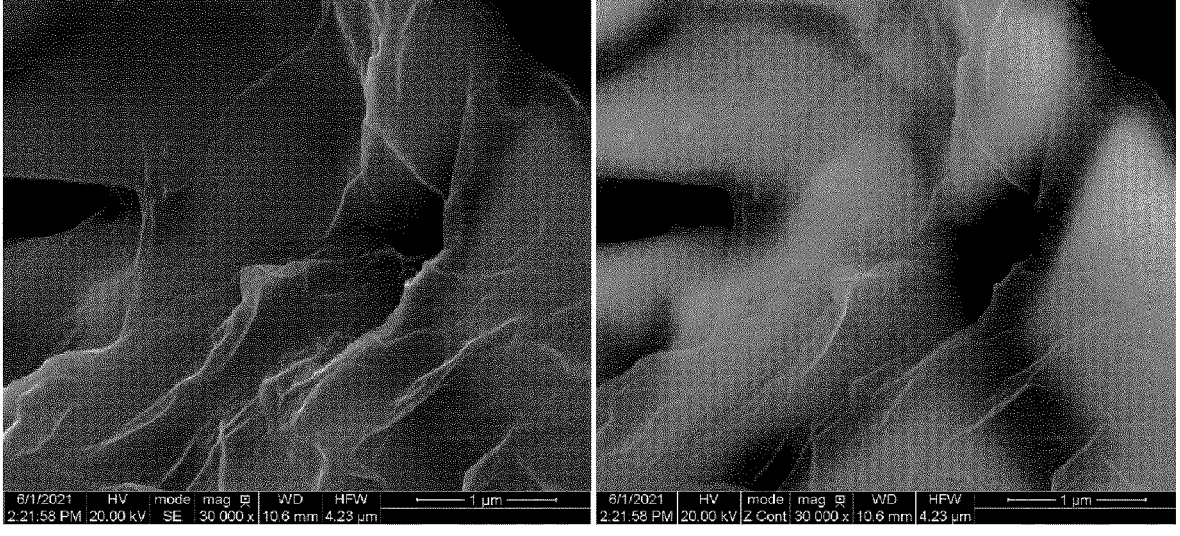
Figure 9A:
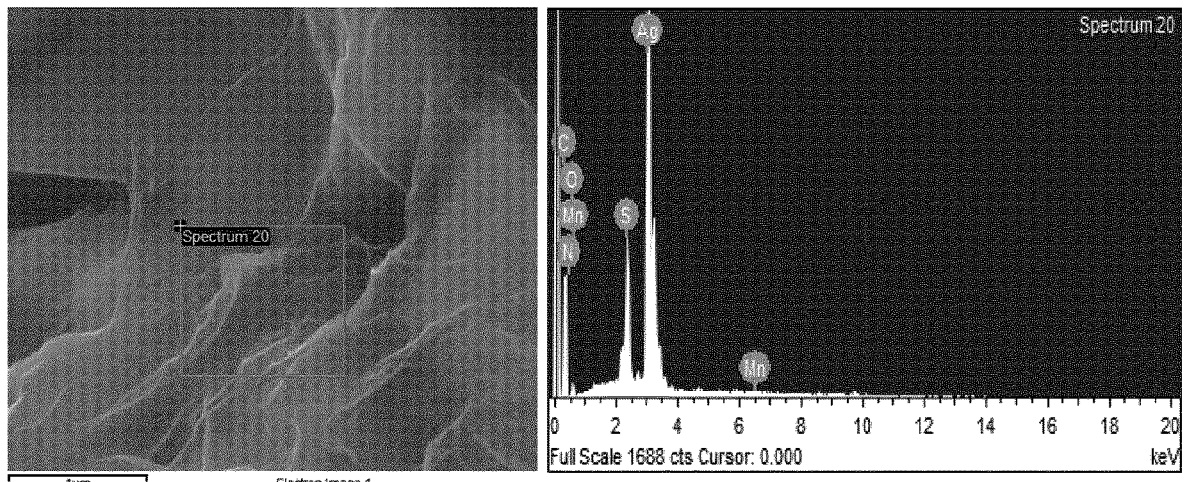
FIGS. 9A and 9B are EDS images and elemental results of GO after contact with silver cations and after purification.
Figure 9B:
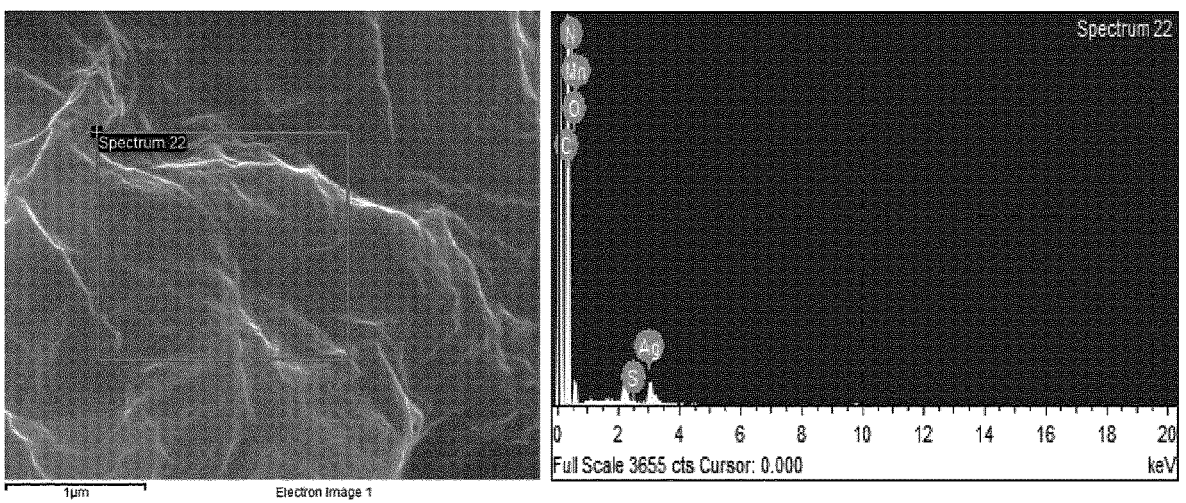

Example 3: Morphological Characterization of Graphene—Silver Cation Nanocomposite The surface morphology of GO-Ag$^+$ nanocomposite was studied by scanning electron microscopy (SEM) and energy-dispersive X-ray spectroscopy (EDS) conducted on surfaces of GO samples, (a) before contact with the silver cations, (b) after contact but before purification (purification being removal of nitrates after supply of Ag$^+$ from silver nitrate), and (c) after purification. The SEM analysis was done in two different modes of SE (scanning electron) and Backscattered-Electron (BSE or Z count); in the second mode, different components with different electron scattering level make different contrasts and provide more surface details (for example, the areas with more silver are brighter). Measurements were conducted on sampes diluted in ethanol. Note that negative results should be read as zero. FIGS. 4A to 4F are SEM (SE) and SEM (Z count) images of GO before contact with the silver cation, and FIGS. 5A to 5C are EDS images and results charts for GO before contact with the silver cation. FIGS. 6A to 6F are SEM (SE) and SEM (Z count) images of GO after contact with the silver cation but before purification, and FIGS. 7A and 7B are EDS images and results charts for GO after contact with the silver cation but before purification. FIGS. 8A to 8D are SEM (SE) and SEM (Z count) images of GO after contact with the silver cation and after purification, and FIGS. 9A and 9B are EDS images and results charts for GO after contact with the silver cation and after purification.

Example 4: Broad-Spectrum Antimicrobial Activity of Graphene-Silver Cation Nanocomposite A macrobroth dilution method was used to determine the MIC of GO-Ag$^+$ nanocomposite against 7 exemplary bacteria and 1 yeast following the Clinical Laboratory Standards Institute (CLSI) M7, M11, and M60 documents. The following organisms were tested:
1. *Streptocococcus pneumoniae* (ATCC® 33400)
2. *Haemophilus influenzae* (ATCC® 51907D-5)
3. *Streptococcus pyogenes* (Group A Streptococcus) (ATCC® 12344D-5)
4. *Moraxella catarrhalis* (ATCC® 19606D-5)
5. *Staphylococcus aureus* (ATCC® 12600)
6. *E. coli* (ATCC® 10798)
7. *Fusobacterium nucleatum* (ATCC® 25586D-5)
8. *Candida albicans* (ATCC® 14053)

GO-Ag$^+$ nanocomposite (Sample #: 09-002-501; Oct. 22, 2020) was initially dissolved in sterile water to a concentration of 2 mg/mL. For *S. pneumoniae*, *S. pyogenes*, *S. aureus*, *M catarrhalis* and *E. coli*, Mueller Hinton Broth was used. For *H. influenzae*, Haemophilus Test Broth was used and for *Fusobacterium nucleatum*, Fastidious Anaerobic Broth was used. The range of concentrations (ug/mL) tested were: 1, 0.5, 0.25, 0.125, 0.0625, 0.031, 0.0156, 0.008 and 0.004 (total of 9 target concentrations). Five replicates at each concentration were tested.

Each organism was prepared to a 0.5 McFarland standard (equivalent to 105 cfu/mL) and inoculated into each tube containing the decreasing concentrations of GO-Ag$^+$ nanocomposite and incubated at 37° C. in 5% CO$_2$ for 18 to 24 hours, with the exception of the *Fusobacterium nucleatum* which was incubated anaerobically. Following incubation, the tubes were examined for turbidity. The lowest concentration showing no turbidity in all 5 replicates was considered as the MIC. A growth control (containing no GO-Ag$^+$ nanocomposite) was used for each organism and each set of tests. A sterility control and growth control were used for each organism to ensure there was no contamination and that growth occurred in the broth medium in the absence of GO-Ag$^+$, respectively.

Results

Table 4 presents results demonstrating the antimicrobial activity of the GO-Ag$^+$ nanocomposite, reflected by the MICs for each of the organisms tested, namely, *Streptococcus pyogenes* (Group A Streptococcus) (ATCC® 12344D-5), *Staphylococcus aureus* (ATCC® 12600), *Streptococcus pneumoniae* (ATCC® 33400), *Moraxella catarrhalis* (ATCC® 19606D-5), *Haemophilus influenzae* (ATCC® 51907D-5), *E. coli* (ATCC® 10798), *Candida albicans* (ATCC® 14053), and *Fusobacterium nucleatum* (ATCC® 25586D-5). The MICs are based on complete inhibition in all 5 replicates where the "X" represents the lowest concentration of the GO-Ag$^+$ nanocomposite at which no visible turbidity was observed.

TABLE 4

| Broad- Spectrum Antimicrobial Activity (MIC) of GO-Ag$^+$ Nanocomposite | | | | | | | | | | |
|---|---|---|---|---|---|---|---|---|---|---|
| | Minimum Inhibitory Concentration (MIC, µg/mL) | | | | | | | | | Growth |
| Organism | 1 | 0.5 | 0.25 | 0.125 | 0.0625 | 0.031 | 0.0156 | 0.008 | 0.004 | Control |
| *Streptococcus pyogenes* (Group A Streptococcus) | | | | | | | X (0.0156) | | | Growth |
| *Staphylococcus aureus* | | | | | | X (0.031) | | | | Growth |
| *Streptococcus pneumoniae* | | | | | | | X (0.0156) | | | |
| *Moraxella catarrhalis* | | | | | | | | X (0.008) | | Growth |
| *Haemophilus influenzae* | | | | | X (0.0625) | | | | | |
| *Escherichia coli* | | | | | | | X (0.0156) | | | Growth |
| *Candida albicans* | | | | | X (0.0625) | | | | | Growth |
| *Fusobacterium nucleatum* | | | | | | Growth | | | | |

Discussion

The results of this evaluation indicate that the GO-Ag$^+$ nanocomposite is capable of inhibiting common aerobic bacteria and yeast at very low concentrations. However, it did not appear to inhibit the anaerobic bacteria used in this evaluation (*Fusobacterium nucleatum*) over the range of concentrations tested. This, however, was due to the Agar used as a medium which negates the activity of Ag$^+$.

GO-Ag$^+$ nanocomposite appears to be active against both gram positive (e.g. *Streptococci* and *Staphylococci*) and gram negative (e.g. *E. coli, H. influenzae, M catarrhalis*) bacteria as well as common yeast (e.g. *Candida albicans*) at extremely low concentrations.

The relatively low concentrations of GO-Ag$^+$ nanocomposite required to achieve an antimicrobial effect are well below the concentration required of commonly used antibiotics to show a similar effect.

Overall, the results of this evaluation demonstrate that GO-Ag$^+$ nanocomposite is a novel compound with broad spectrum antibacterial, antiviral, and antifungal activity at extremely low concentrations of 0.008-0.0625 µg/mL.

Example 5: Antimicrobial Activity of Graphene-Silver Cation Nanocomposite Against Antimicrobial Resistant and Multidrug Resistant Patehogens The efficacy of the GO-Ag$^+$ nanocomposite was further tested against a broad range of exemplary, non-limiting, antimicrobial resistant (AMR) and multidrug resistant (MDR) organisms, that include:
1. Gram Negative Bacteria:
    *Pseudomonas aeruginosa* (2 separate isolates)
    *E. coli* (Extended Spectrum Beta-Lactamase producer [ESBL])
    *E. coli* (Carbapenem Resistant [CRO])
    *Klebsiella pneumoniae* (ESBL)
    *Klebsiella pneumoniae* (CRO)

20

*Enterobacter aerogenes*
*Stenotrophomonas maltophilia*
2. Gram Positive Bacteria:
    Hospital Acquired-Methicillin Resistant *Staphylococcus aureus* (HA-MRSA)
    Community Acquired-Methicillin Resistant *Staphylococcus aureus* (CA-MRSA)
    Vancomycin Resistant *Enterococcus faecium* (VRE)
    Penicillin-resistant *Streptococcus pneumoniae*

The same methodology was used as described in Example 4 and the results are presented in Table 5. In particular, GO-Ag$^+$ nanocomposite (Sample #: 09-002-501; Oct. 22, 2020) was initially dissolved in sterile water to a concentration of 2 mg/mL. Mueller Hinton (MH) Broth was used for all organisms. The range of concentrations (µg/mL) tested were: 1, 0.5, 0.25, 0.125, 0.0625, 0.031, 0.0156, 0.008 and 0.004 (total of 9 target concentrations). Five replicates at each concentration were tested.

Each organism was prepared to a 0.5 McFarland standard (equivalent to 10$^5$ cfu/mL) and inoculated into each tube containing the decreasing concentrations of GO-Ag$^+$ and incubated at 37° C. in 5% $CO_2$ for 18 to 24 hours. Following incubation, the tubes were examined for turbidity. The lowest concentration showing no turbidity in all 5 replicates was considered as the MIC. Sub-cultures were performed to confirm a 99.9% reduction in growth for each organism compared to the growth control. A growth control (containing no GO-Ag$^+$) was used for each organism and each set of tests. A sterility control and growth control were used for each organism to ensure there was no contamination and that growth occurred in the broth medium in the absence of GO-Ag$^+$, respectively.

Table 5 presents results demonstrating the antimicrobial activity of the GO-Ag$^+$ nanocomposite, reflected by the MICs for each of the AMR organisms tested, namely, *Serratia marcescent* (S.mar), *Pseudomonas aeruginosa* (P.aer 1), *Pseudomonas aeruginosa* (P.aer 2), *Escherichia coli* (ESBL), *Escherichia coli* (CRO), *Klebsiella pneumonia* (ESBL), *Klebsiella pneumonia* (CRO), *Enterobacter aerogenes*, *Stenotrophomonas maltophilia*, *Methicillin Resistant Staphylococcus aureus* (MRSA), *CA-Methicillin Resistant Staphylococcus aureus* (MRSA), *Vancomycin Resistant Enerococcus faecium* (VRE), *Penicillin Resistant Strepto-*

*coccus pneumoniae.* The averaged MIC values (measured in μg/mL) of the GO-Ag⁺ nanocomposite against the exemplary organisms tested are presented. The MICs are based on complete inhibition in all 5 replicates where the "X" represents the lowest concentration of the GO-Ag⁺ nanocomposite at which no visible turbidity was observed.

The results of this evaluation demonstrate the efficacy of the GO-Ag⁺ nanocomposite against exemplary known AMR and MDR pathogens, including ESKAPE pathogens, which are associated with a number of difficult to treat clinical infections including those involving the respiratory tract, urinary tract, skin and soft tissues, and bacteremia at very low concentrations. The unexpectedly low MIC values ranged from 0.008 to 0.031 μg/mL (Table 5). Based on the previous evaluation of GO-Ag⁺ against fully susceptible organisms (i.e. *E. coli, S. aureus, Streptococcus pneumoniae*) (see Example 4), the MICs for the AMR strains were comparable or a single dilution higher.

Example 6: Comparison of Antimicrobial Efficacy and Synergistic Effect

The antimicrobial efficacy of the GO-Ag⁺ nanocomposite, according to embodiments disclosed herein, was compared to the antimicrobial efficacy of previously described nanocomposites. As presented in Table 6, a comparison of the MICS of previously described nanocomposites, demonstrates an unexpected improved efficacy exhibited by the GO-Ag⁺ nanocomposite over previously described nanocomposites.

Table 6 presents a comparison of the antimicrobial activity of the GO-Ag⁺ nanocomposite for various pathogens compared to the antimicrobial efficacy of known metals and graphene composites as reported in: (a) Zhong, L. and Yun, K. "Graphene oxide-modified ZnO particles: synthesis, characterization antibacterial properties." International Journal of Nanomedicine Spec. Iss. 10, 79-92; (b) Matar, Susan A. et al. "The antibacterial biofilm activity of metal-doped

TABLE 5

| Broad- Spectrum Antimicrobial Activity (MIC) of GO-Ag⁺ Nanocomposite | | | | | | | | | | |
|---|---|---|---|---|---|---|---|---|---|---|
| | Minimum Inhibitory Concentration (MIC, μg/mL) | | | | | | | | | Growth |
| Organism | 1 | 0.5 | 0.25 | 0.125 | 0.0625 | 0.031 | 0.0156 | 0.008 | 0.004 | Control |
| Gram Negatives | | | | | | | | | | |
| *Serratia marcesens* (S. mar) | | | | | | | X (0.0156) | | | Growth |
| *Pseudomonas aeruginosa* (P. aer 1) | | | | | | | X (0.0156) | | | Growth |
| *Pseudomonas aeruginosa* (P. aer 2) | | | | | | | X (0.0156) | | | |
| *Escherichia coli* (ESBL) | | | | | | X (0.031) | | | | Growth |
| *Escherichia coli* (CRO) | | | | | X (0.0625) | | | | | Growth |
| *Klebsiella pneumoniae* (ESBL) | | | | | | X (0.031) | | | | Growth |
| *Klebsiella pneumoniae* (CRO) | | | | | X (0.0625) | | | | | Growth |
| *Enterobacter aerogenes* | | | X (0.25) | | | | | | | Growth |
| *Stenotrophomonas maltophilia* | | | | | | X (0.031) | | | | Growth |
| Gram Positives | | | | | | | | | | |
| HA- Methicillin Resistant *Staphylococcus aureus* (MRSA) | | | | | X (0.0625) | | | | | Growth |
| CA- Methicillin Resistant *Staphylococcus aureus* (MRSA) | | | | | | X (0.031) | | | | Growth |
| Vancomycin Resistant *Enterococcus faecium* (VRE) | | | | | | X (0.031) | | | | Growth |
| Penicillin Resistant *Streptococcus pneumoniae* | | | | | | | | X (0.008) | | Growth | mullite ceramics against pathogenic bacteria." African Journal of Microbiology Research 7 (23), June 2013, 2939-2947; (c) Salman, Halah Dawood, "Evaluation and Comparison the Antibacterial Activity of Silver Nano Particles (AgNPs) and Silver Nitrate (AgNO₃) on Some Pathogenic Bacteria." Journal of Global Pharma Technology, December 2016; (d) Panacek et al. "Silver colloid nanoparticles: Synthesis, characterization and their antibacterial activity." Journal of Physical Chemistry B 110 (33), 16248-16253; (e) Anni, Feng et al. "Facile Synthesis of Silver nanoparticles with pathogens, the MIC of the GO-Ag⁺ nanocomposite, according to embodiments disclosed herein, is at least 100× to 10,000× lower than the MIC of previously described nanocomposites.

Moreover, these data demonstrate the unexpected synergistic effect of graphene oxide with cationic silver (GO-Ag⁺ complex) when considering broad spectrum antimicrobial efficacy.

TABLE 6

| Comparison of Antimicrobial Efficacy and Synergistic Effect | | | | | | |
|---|---|---|---|---|---|---|
| | MIC (µg/mL) | | | | | |
| Organism | Graphene Oxide (GO) | Silver Nanoparticles-Graphene Oxide (AgNPGO) | Silver Nitrate (AgNO₃) | Silver Nanoparticles (AgNP) | Zinc Oxide-Graphene Oxide (ZnO•GO) | Graphene Oxide-Cationic Silver (GOAg⁺) |
| *Streptococcus pyogenes* | | | 80 $^c$ | 50 $^c$ | | 0.0156 |
| *Staphylococcus aureus* | >60 $^g$ | 256 $^e$ | 80 $^c$ | 60 $^c$ | | 0.031 |
| | | | 50 $^b$ | 7 | | |
| | | 30 $^g$ | 9.8 $^f$ | 54 $^d$ | | |
| *Moraxella catarrhalis* | | | | | | 0.0156 |
| *Haemophilus influenzae* | | | | | | 0.008 |
| *Escherichia coli* | 12.5 $^a$ | 512 $^e$ | 130 $^c$ | 70 $^c$ | 6.25 $^a$ | 0.0625 |
| | | | | 3 | | |
| | >60 $^g$ | 15 $^g$ | 4.9 $^f$ | 27 $^d$ | | |
| *Candida albicans* | | | 4.9 $^f$ | | | 0.0156 |
| *Fusobacterium nuclatum* | | | | | | 0.0625 |
| *Klebsiella pneumoniae* | | | 140 $^c$ | 70 $^c$ | | |
| | | | 4.9 $^f$ | | | |
| *Salmonella typhi* | 12.5 $^a$ | | 110 $^c$ | 70 $^c$ | 6.25 $^a$ | |
| *Vibrio cholerae* | | | 70 $^c$ | 50 $^c$ | | |
| *Bacillus subtilis* | 25 $^a$ | | | | 12.5 $^a$ | |
| *Enterococcus faecalis* | 50 $^a$ | 30 $^g$ | | | 25 $^a$ | |
| | >60 $^g$ | | | | | |
| *Staphylococcus aureus* (MRSA) | >60 $^g$ | 15 $^g$ | | | | 0.031 |

$^a$ Zhong, L. and Yun, K. "Graphene oxide-modified ZnO particles: synthesis, chracterization antibacterial properties." International Journal of Nanomedicine Spec. Iss. 10, 79-92;
$^b$ Matar, Susan A. et al. "The antibacterial biofilm activity of metal-doped mullite ceramics against pathogenic bacteria." African Journal of Microbiology Research 7 (23), June 2013, 2939-2947;
$^c$ Salman, Halah Dawood, "Evaluation and Comparison the Antibacterial Activity of Silver Nano Particles (AgNPs) and Silver Nitrate (AgNO₃) on Some Pathogenic Bacteria." Journal of Global Pharma Technology, December 2016;
$^d$ Panacek et al. "Silver colloid nanoparticles: Synthesis, characterization and their antibacterial activity." Journal of Physical Chemistry B 110 (33), 16248-16253;
$^e$ Anni, Feng et al. "Facile Synthesis of Silver nanoparticles with High Antibacterial Activity." Materials 11 (12), December 2018;
$^f$ Ulkuseven, Bahri et al. "Synthesis, Characterization and antimicrobial Activity of d8-10 Metal Complexes of soe 2-substituted-1H-Benzimidazoles." Metal-Based Drugs 6 (3), 1999;
$^g$ Mazarin de Moraes, A. C. et al. "Graphene oxide-silver nanocomposite as a promising biocidal agent against methicillin-resistant *Staphylococcus aureus*." Int J Nanomedicine 10: 6847-6861, 2015.

High Antibacterial Activity." Materials 11 (12), December 2018; (f) Ulkuseven, Bahri et al. "Synthesis, Characterization and antimicrobial Activity of d8-10 Metal Complexes of nine 2-substituted-1H-Benzimidazoles." Metal-Based Drugs 6 (3), 1999; (g) Mazarin de Moraes, A. C. et al. "Graphene oxide-silver nanocomposite as a promising biocidal agent against methicillin-resistant *Staphylococcus aureus*." Int J Nanomedicine 10:6847-6861, 2015.

Referring to the comparative data presented in Table 6, these data demonstrate that the GO-Ag⁺ nanocomposite, according to embodiments disclosed herein, significantly outperform graphene oxide (GO), graphene oxide-silver nanoparticle (AgNPGO), silver nitrate (AgNO₃), silver nanoparticles (AgNP), and zinc oxide-graphene oxide (ZnO.GO). As reflected by the MICs for representative Example 7: Virucidal Activity of Graphene-Silver NP Nanocomposite The virucidal activity of GO-AgNP nanocomposite was assessed for comparison purposes.

Preparation of GO-AgNP Nanocomposite

To synthesize Ag-doped GO nanosheets, 0.1 g dried pristine GO powder was dispersed in 30 mL DI water in a 100 mL Erlenmeyer flask using a bath sonicator for 30 min. The pH of the GO suspension was adjusted at 10 using NaOH solution (0.1 M). Then, 2 mL of the AgNO3 solution (0.25 M) was added to the previous suspension under stirring (400 rpm). Next, 20 mL DI water was added to the previous suspension to reduce the viscosity of the solution. The mixture was stirred for 20 h at 60° C.

Method for SARS-CoV-2 Replication/Inhibition Tests

The virucidal activity of GO-AgNP nanocomposite was tested at the ImPaKt Facility at Western University. The GO-AgNP nanocomposite was in the form of a thick viscosity paste which was applied to the bottom surface of a 12-well dish using a flat edge weight spoon.

SARS-CoV-2 Wuhan strain viruses were serially diluted 4 times to produce infectious units of approximately 200,000 infectious units (IU), 20,000 IU, 2,000 IU, and 200 IU per 20 µL. 200 µL of the SARS-CoV-2 dilutions were overlaid onto the GO-AgNP treated and untreated surfaces. After 1 hour and 12 hours incubation of virus with the treated surfaces, 20 µL of supernatant in each well was added to wells of a new 96 well plates containing approximately 20,000 Vero cells in DMEM media. The final multiplicity of infection was 2.0, 0.2, 0.02, and 0.002 infectious units per cell for each viral dilution. Viral cytopathic effects (vCPE) on cells were observed within a day and vCPE was measured at day 3.

Results from SARS-CoV-2 Replication/Inhibition Tests

The results of the replication/inhibition tests are presented in Table 7.

At 2,000 IU, the GO-AgNP nanocomposite had approximately 20-30% protective effect on the SARS-CoV-2 infection of VERO E6 cells. At both 200 IU and 20 IU, approximately 10-20% protective effect was observed on the SARS-CoV-2 infection of VERO E6 cells. At 20,000 IU of virus, no protective effect was observed. At 12 hours, clear viral activity was significantly decreased in both treated and untreated conditions. No difference was observed between treated and untreated surfaces.

TABLE 7

Viral Cytopathic Effect (vCPE) of GO-AgNP nanocomposite on SARS-COV-2 Infected VERO E6 Cells

| P2-1 hr treatment | | | |
|---|---|---|---|
| 20,000 IU | +++++ | +++++ | +++++ |
| 2,000 IU | +++ | +++ | +++ |
| 200 IU | +++ | +++ | +++ |
| 20 IU | ++ | ++ | ++ |
| 0 | N.I. | N.I. | N.I. |
| 1 hr-no treatment | | | |
| 20,000 IU | +++++ | +++++ | +++++ |
| 2,000 IU | +++++ | +++++ | +++++ |
| 200 IU | ++++ | ++++ | ++++ |
| 20 IU | ++++ | ++++ | ++++ |
| 0 | N.I. | N.I. | N.I. |

Key:

| | |
|---|---|
| +++++ | 80-100% Infected cells |
| ++++ | 60-80% Infected cells |
| +++ | 40-60% Infected cells |
| ++ | 20-40% Infected cells |
| + | 1-10% Infected cells |
| N.I. | 0% Infected cells |

Example 8: Graphene—Silver Cation Nanocomposite Formulation for Surface Coating

To apply the GO-Ag⁺ nanocomposite to a surface, the GO-Ag⁺ nanocomposite was further formulated as a suspension. A mixture of ethanol and deionized water (DI) was used. In 100 mL of suspension, 60 to 70 mL of ethanol and 30 to 40 mL of DI water were used as the diluent. The GO-Ag⁺ nanocomposite was suspended in the diluent at a concentration of 0.1 to 5 g/L making a dispersion. The resulting formulation comprising GO-Ag⁺ nanocomposite was applied to surfaces and filter media by either dip or spray coating and then air-dried or thermally-dried to fix the GO-Ag⁺ nanocomposite onto the media.

Example 9: Morphological Characterization of Graphene—Silver Cation Nanocomposite Coated Surface The surface morphology of fabric samples coated with GO-Ag⁺ nanocomposite, applied by dip coating, was studied by scanning electron microscopy (SEM), field emission SEM (FE-SEM) coupled with an energy-dispersive x-ray (EDX) spectroscopy.

EDX elemental analysis was performed to evaluate the amount of carbon, oxygen, silver, etc. on the surface of the fabric (polyurethane) after dip coating with the GO-Ag⁺ nanocomposite formulation prepared by the method described in Example 8. The formulation was applied at two different concentrations, low loading and high loading (0.5 g/L and 5 g/L).

For FE-SEM-EDX analysis, the sample coated fabric (1 cm by 1 cm) was cut and coated with a thin layer of gold using a metal vapor deposition technique to make the surface of the fabric conductive. Then, the analysis was conducted on the sample. After selecting an appropriate area of the fabric with a proper magnification, elemental mapping was done using EDX.

Figure 10A:
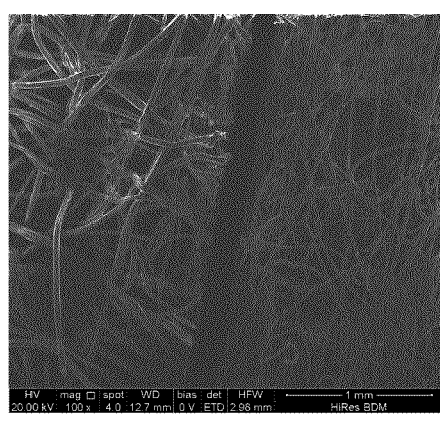
FIGS. 10A, 10B, and 10C are SEM images of both sides of a fabric sample coated with GO-$Ag^+$ nanocomposite at a high loading concentration of 5 g/L.
Figure 10B:
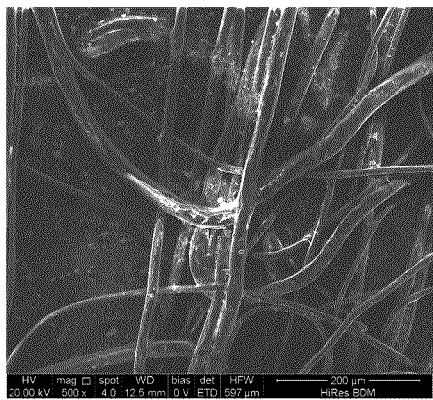
Figure 10C:
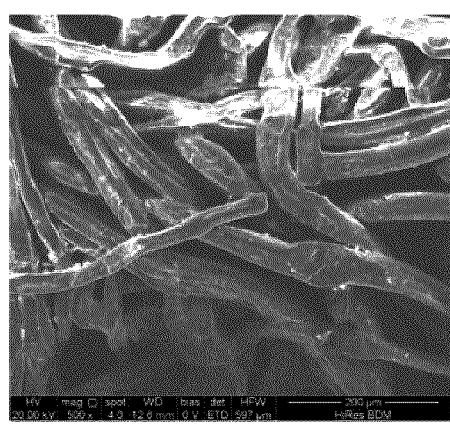
Figures 11A, 11B, 11C:
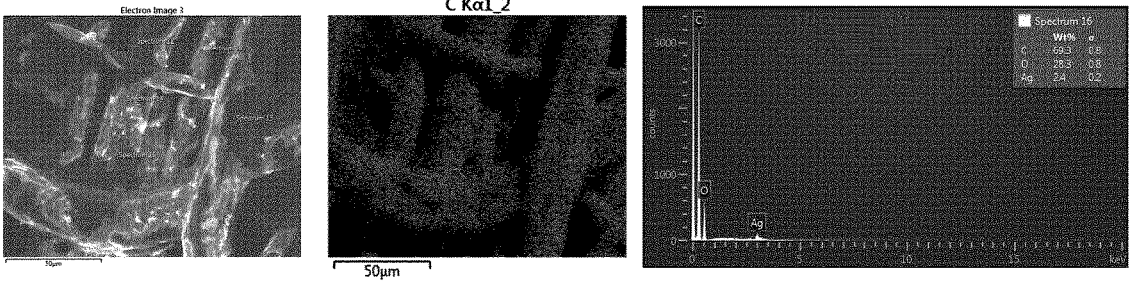
FIGS. 11A, 11B, 11C, 11D, 11E, 11F are EDX analysis images of the fine side of a fabric sample with GO-$Ag^+$ nanocomposite at a high loading concentration of 5 g/L.
Figures 11D, 11E, 11F:
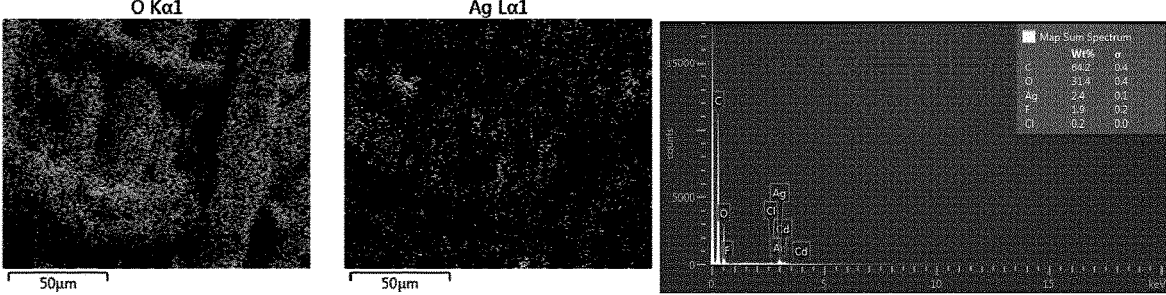
Figures 12A, 12B, 12C:
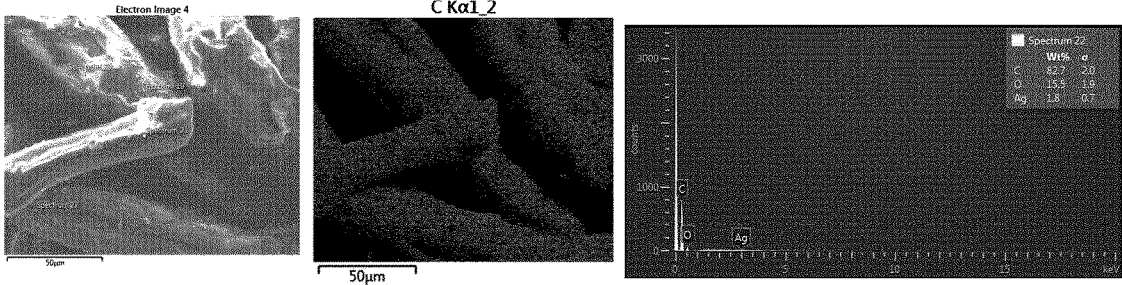
FIGS. 12A, 12B, 12C, 12D, 12E, 12F are EDX analysis images of the rough side of a fabric sample with GO-$Ag^+$ nanocomposite at a high loading concentration of 5 g/L.
Figures 12D, 12E, 12F:
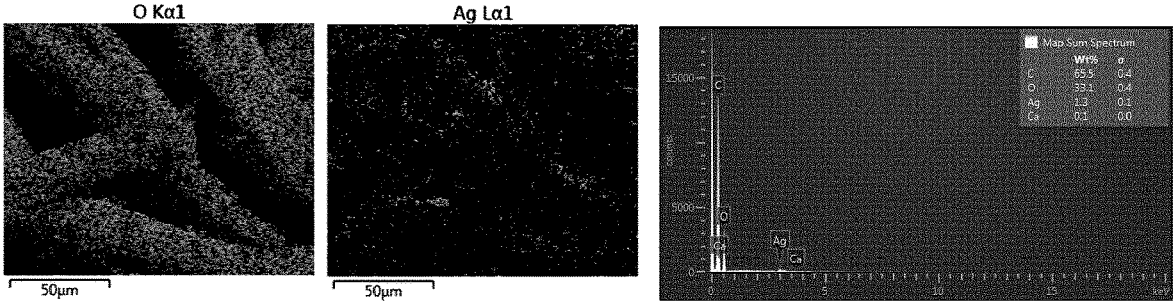
Figure 16A:
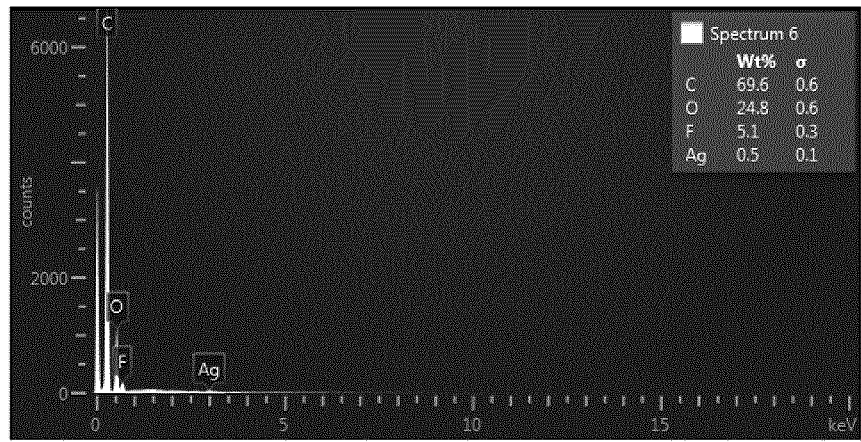
FIGS. 16A and 16B show the peak identification for the targeted elements from FIG. 15.
Figure 16B:
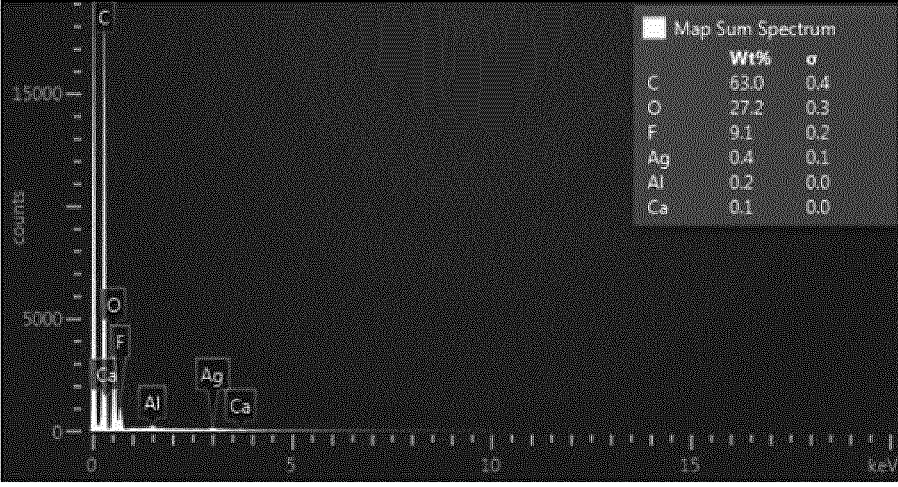
Figures 17A, 17B, 17C:
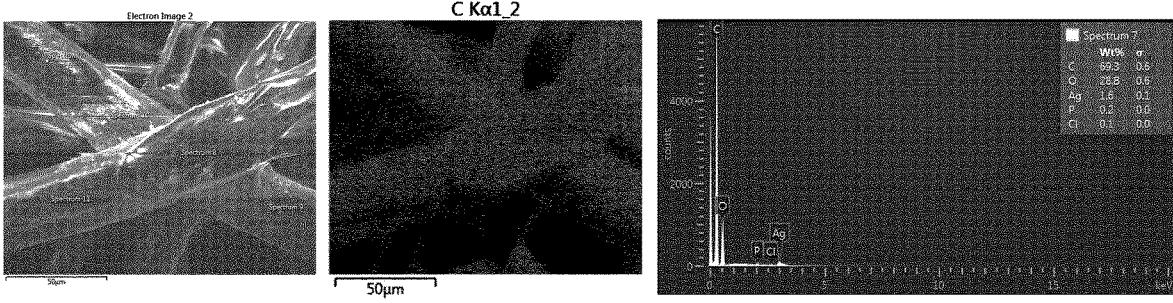
FIGS. 17A, 17B, 17C, 17D, 17E, 17F are EDX analysis images of the rough side of a fabric sample with GO-$Ag^+$ nanocomposite at a low loading concentration of 0.5 g/L.
Figures 17D, 17E, 17F:
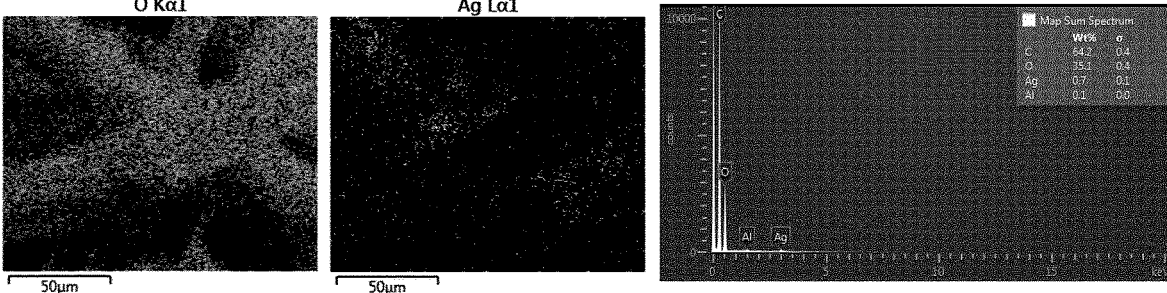

As shown in FIGS. 10A, 10B, 10C, each fabric sample has two different sides, a rough side and a fine side. The rough side appeared to be more hydrophobic with thicker fabrics while the fine side was hydrophilic with thinner fabrics. That is why the concentration of the Ag element on the finer side was greater as the coating is in a water dispersion and adheres to the hydrophilic side. Also, the map of the surface Ag showed a relatively uniform distribution which demonstrates that the coating is dispersed well in the water/ethanol medium and that dip coating is an effective technique for coating mask material.

As shown in FIGS. 11 to 18, the elemental composition of the sides of each coated fabric sample was also determined by EDX analysis. As shown in FIGS. 11, 12, 15, 17, each color in EDX-maps corresponds to a certain element. Since EDX analyzes the the sample depth to about 1-3 um, black areas with no Ag are indicative of waves or texture in the fabric.

Example 10: Virucidal Activity of Graphene-Silver Cation Nanocomposite

Viral titer reduction studies with SARS-CoV-2 were conducted for N-95 mask material coated with the GO-Ag⁺ nanocomposite. Coating with GO-Ag⁺ nanocomposite was found to effectively reduce virus activity by 99% after 2 hours of exposure.

Material Preparation

The coated N-95 mask materials were prepared according to the method described in Examples 1 and 8 herein. The materials were prepared 5 weeks prior to virucidal testing.

The coated N-95 mask material appeared dark gray in color. Uncoated N-95 material was used as a control. The materials were autoclaved to sterilize before testing at 121° C. for 30 min prior to the test analyses. After sterilization, inside a biological safety cabinet (BSC), the material was cut into ~0.5×0.5 cm squares and placed into sterile 1.5 ml tubes.

SARS-CoV-2 Preparation and Testing

The SARS-CoV-2 virus stock at a titer of $10^{5.8}$ infectious units (IU)/ml was diluted to $10^{2.9}$ (IU)/ml. A volume of 500 ml of the diluted viral stock was added to a 1.5 ml tube containing the square of the coated material. The tube containing the virus and coated material was placed on a tube rotator for 2 hrs at 22° C. Untreated material (0-001-011) exposed to viral supernatant was used as a control. Collected supernatants were diluted 100-fold to dilute any chemicals/materials that may have been released from the coated material during incubation. The collected supernatants (diluted 100-fold) were further serially diluted from 1:100 to 1:100,000 and then added to 20,000 Vero E6 cells in 96 well flat-bottom plates.

The 1:100 dilution of the virus stock infecting 20,000 cells represents a multiplicity of infection (MOI) of 0.02. Infection of the Vero E6 cells was monitored by viral cytotoxicity. Cell toxicity of the supernatants-derived material in the absence of virus (diluted 1:100) was measured visually.

Results

As shown in Table 8, viral titers were reduced by 2 Logs corresponding to 99% reduction in infectious virus after 2 hours of exposure to N-95 respirator material coated with GO-Ag$^+$ nanocomposite. Exposure to control mask material, i.e., untreated N-95 material, resulted in no reduction of viral titers. All experiments were performed in triplicate. Variance in the results was less than 5% and reported as 99% reduction in infectious virus (or 99% in viricidal activity).

TABLE 8

Virudical Activity of GO-Ag Cation Nanocomposite on SARS-COV-2 Infected VERO E6 Cells

| Sample N-95 Material | Viral Titer | Reduction Factor (Log10) v. Control (Post 2 HRs Exposure) | % Viral Reduction |
|---|---|---|---|
| GO-Ag+ Sample 1 | $10^{2.8}$ | 2 | 99% |
| GO-Ag+ Sample 2 | $10^{2.8}$ | 2 | 99% |
| Untreated Control | $10^{3.8}$ | 0 | 0% |

* Diluted control virus after dilution resulted in a TCID 50/ml of $10^{3.8}$

Example 11: Enhanced Microbe Filtration Efficiency

According to certain embodiments described herein, the GO-Ag$^+$ nanocomposite can be formulated for use in PPE, air filtration (HVAC) systems, and other airflow membranes and filters, to reduce or eliminate the activity of the microbial pathogens. The efficacy of PPE and other airflow membranes/filter systems relies on the filtration efficiency (FE) against microbial pathogens.

Without being bound by theory, it is contemplated that the hydrophilicity of the GO-Ag$^+$ nanocomposite attracts, retains, and immobilizes microbes on the treated surface to inhibit passage through the filtering device. Enhancing the filtration efficiency of a substrate, such as a medical mask, in combination with deactivating/killing the microbe, results in improved performance of the filtering device.

The ability of the GO-Ag$^+$ nanocomposite to improve the filtration efficiency of a 3 or 4-ply medical mask was tested against a representative bacterial and viral pathogen using a standard industrial test method.

Material Preparation

The coated N-95 mask materials were prepared according to the method described in Examples 1 and 6 herein. The materials were prepared 5 weeks prior to virucidal testing.

The coated N-95 mask material appeared dark gray in color. Uncoated N-95 material was used as a control. The materials were autoclaved to sterilize before testing at 121° C. for 30 min prior to the test analyses.

Bacterial Filtration Efficiency Test

A Bacterial Filtration Efficiency (BFE) test was completed at an increased challenge level to allow for measurement of filtration efficiency greater than what can be measured using the standard BFE procedure. Testing was completed according to the standard ASTM F2101 (Standard Test Method for Evaluating the Bacterial Filtration Efficiency (BFE) of Medical Face Mask Materials, Using a Biological Aerosol of *Staphylococcus aureus*, ASTM International, West Conshohocken, PA, 2001) whereby a suspension of *S. aureus* (*Staphylococcus aureus* ATCC 6538) bacterial challenge was aerosolized using a nebulizer with a target delivery of greater than $5 \times 10^6$ colony forming units (CFU). The aerosolized suspension was drawn through the user side face of the test article at a fixed flow rate of 28.3 LPM into all-glass impingers (AGIs) for the collection of viable microbes. The area tested was ~38.5 cm$^2$. The challenge was delivered for 5 minutes and sampling was conducted for 6 minutes total to ensure the aerosol chamber was cleared. Surviving microbes collected in the AGIs were enumerated using a membrane filtration procedure. The mean particle size (MPS) was determined using the procedure outlined in ASTM F2101, with the collection of a *S. aureus* challenge using a six-stage Andersen sampler at 28.3 LPM. Uncoated controls were performed to ensure repeatability and reliability.

The challenge level for these tests was determined at $6.9667 \times 10^{\wedge}6$ CFU of *S. aureus* having a mean particle size of 2.83 μm.

Viral Filtration Efficiency Test

A Viral Filtration Efficiency (VFE) test using MS2 bacteriophage was completed at an increased challenge level to allow for measurement of filtration efficiency greater than what can be measured using the standard VFE procedure. Testing was completed according to the standard ASTM F2101 (Standard Test Method for Evaluating the Bacterial Filtration Efficiency (BFE) of Medical Face Mask Materials, Using a Biological Aerosol of *Staphylococcus aureus*, ASTM International, West Conshohocken, PA, 2001) whereby a suspension of MS2 bacteriophage (MS2 Bacteriophage ATCC 15597-B1) challenge was aerosolized using a nebulizer with a target delivery of greater than $1 \times 10^7$ plaque-forming units (PFU). The aerosolized suspension was drawn through the user side face of the test article at a fixed flow rate of 28.3 LPM into all glass impingers (AGIs) for the collection of viable microbes. The challenge was delivered for 5 minutes and sampling was conducted for 6 minutes total to ensure the aerosol chamber was cleared. Surviving microbes collected in the AGIs were enumerated using a single agar layer procedure using an *E. coli* host to allow visualization of clearing zones (plaques) representing viable MS2 bacteriophage that had passed through the mask. The mean particle size (MPS) was determined using the procedure outlined in ASTM F2101, with the collection of a MS2 bacteriophage challenge using a six-stage Andersen sampler at 28.3 LPM. Controls were performed to ensure repeatability and reliability.

The challenge level for these tests was determined at $2.2933 \times 10^{\wedge}7$ CFU of MS2 bacteriophage having a mean particle size of 2.76 μm.

29

30

Results

The % BFE or % VFE was calculated as follows:

$$\% \; BFE \; \text{or} \; \% \; VFE = \frac{C - T}{C} \times 100$$

Where: C=Challenge Level

T=Total CFU recovered downstream of test article

The MPS was determined as follows:

$$MPS = \frac{\begin{array}{c}(P1 \times C1) + (P2 \times C2) + (P3 \times C3) + \\ (P4 \times C4) + (P5 \times C5) + (P6 \times C6)\end{array}}{C1 + C2 + C3 + C4 + C5 + C6}$$

Where:

Px=50% effective cut-off diameter for the $X^{th}$ stage as indicated by the manufacturer Cx=raw count (on stages 1 and 2) or the "probable hit" count determined using the positive hold conversion chart from the cascade impactor manual (for stages 3 through 6) on the $X^{th}$ stage As presented in Table 9, the masks coated with GO-Ag⁺ nanocomposite removed 98.9% more bacteria and 97.8% more viruses than the uncoated mask. It resulted in a mask with over 99.99% viral and bacterial filtration efficiency.

TABLE 9

Bacterial Filtration Efficiency (Uncoated vs GO-Ag⁺ nanocomposite Coated PPE Mask)

| S. aureus | Total CFU Recovered-Averaged from 3 tests | Bacterial Filtration Efficiency (%) |
|---|---|---|
| Uncoated | 38,500 | 99.4474% |
| GO-Ag⁺ nanocomposite-Coated | 410 | 99.9941% |

TABLE 10

Viral Filtration Efficiency (Uncoated vs GO-Ag⁺ nanocomposite Coated PPE Mask)

| MS2 Bacteriophage | Total CFU Recovered-Averaged from 3 tests | Viral Filtration Efficiency (%) |
|---|---|---|
| Uncoated | 76,667 | 99.6657% |
| GO-Ag⁺ nanocomposite-Coated | 1,683 | 99.9927% |

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The invention claimed is:

1. An antimicrobial nanocomposite comprising graphene oxide (GO) and silver cations (Ag⁺) bound to the GO as Ag(1)-complexes, wherein the silver cations (Ag⁺) are bound to the GO by complex bonds, and wherein the nanocomposite is effective at killing coronavirus.

2. The nanocomposite according to claim 1 wherein the complex bonds are chelated bonds or coordinate covalent bonds.

3. The nanocomposite according to claim 1, wherein the nanocomposite comprises between 3-80% w/w, 10-20% w/w, or 4-8% w/w of silver cations bound to the GO.

4. The nanocomposite according to claim 1, further comprising silver nanoparticles covalently bound to the GO of the nanocomposite.

5. The nanocomposite according to claim 4, wherein the silver cation and silver nanoparticles are present in a ratio of 10:1 to 15:1.

6. The nanocomposite according to claim 4 wherein the silver cations bound to the GO comprises about 90-99% silver cations (Ag⁺) in an Ag(1)-complex form and about 1-10% silver nanoparticles in a clustered Ag(0)-nanoparticle form.

7. The nanocomposite according to claim 1, further comprising copper cations ($Cu^{2+}$), or zinc cations ($Zn^{2+}$).

8. The nanocomposite according to claim 1, wherein the nanocomposite has a particle size ranging from 2 to 10 μm.

9. The nanocomposite according to claim 1, wherein said coronavirus is Covid-19 coronavirus, SARS coronavirus, MERS coronavirus, or SARS-CoV-2 virus.

10. An antimicrobial formulation comprising the nanocomposite according to claim 1, and a solvent, a carrier, a diluent, and/or a dispersant.

11. The antimicrobial formulation according to claim 10, wherein the formulation has a nanocomposite concentration of 40 mg/L to 5 g/L.

12. The antimicrobial formulation according to claim 10, wherein the formulation is a liquid spray, mist, foam, dip-coat bath, wipe, or coating.

13. The antimicrobial formulation according to claim 10, wherein the formulation is applied to a face mask, personal protective equipment (PPE), environmental cleaning wipes, counters, door handles, walls, or airflow membranes and filters to provide a coating thereon.

14. The antimicrobial formulation according to claim 12, wherein the coating has a thickness from about 5 nm to about 5 μm, from about 100 nm to about 3 μm, from about 200 nm to about 2 μm, from about 300 nm to about 1.5 μm, or from about 500 nm to about 1.0 μm.

15. A method for conferring antimicrobial activity to a substrate, comprising:

dispersing the nanocomposite of claim 1 in ethanol, or deionized water, or a mixture of deionized water and ethanol to provide a nanocomposite dispersion;

applying the nanocomposite dispersion to a substrate to provide the nanocomposite dispersed on the substrate; and fixing the nanocomposite dispersed on the substrate by air or heat drying.

16. The method according to claim 15, wherein the nanocomposite dispersion is applied to the substrate by spray coating or dip coating.

17. The method according to claim 15, wherein the nanocomposite dispersion is applied to said substrate to provide a coating that ranges in thickness from about 5 nm to about 5 μm, from about 100 nm to about 3 μm, from about 200 nm to about 2 μm, from about 300 nm to about 1.5 μm, or from about 500 nm to about 1.0 μm.

\* \* \* \* \*